US012036225B2

(12) United States Patent
Garey

(10) Patent No.: US 12,036,225 B2
(45) Date of Patent: Jul. 16, 2024

(54) USE OF IBEZAPOLSTAT TO PROMOTE MICROBIOME HEALTH

(71) Applicant: Acurx Pharmaceuticals, Inc., Staten Island, NY (US)

(72) Inventor: Kevin Garey, Houston, TX (US)

(73) Assignee: Acurx Pharmaceuticals, Inc., Staten Island, NY (US)

( * ) Notice: Subject to any disclaimer, the term of this patent is extended or adjusted under 35 U.S.C. 154(b) by 0 days.

(21) Appl. No.: 17/842,374

(22) Filed: Jun. 16, 2022

(65) Prior Publication Data

US 2022/0409625 A1    Dec. 29, 2022

Related U.S. Application Data

(60) Provisional application No. 63/264,052, filed on Nov. 15, 2021, provisional application No. 63/263,556, filed on Nov. 4, 2021, provisional application No. 63/236,972, filed on Aug. 25, 2021, provisional application No. 63/211,320, filed on Jun. 16, 2021.

(51) Int. Cl.
*A61K 31/522* (2006.01)
*A61P 31/04* (2006.01)

(52) U.S. Cl.
CPC ............ *A61K 31/522* (2013.01); *A61P 31/04* (2018.01)

(58) Field of Classification Search
CPC .............................. A61K 31/522; A61P 31/04
See application file for complete search history.

(56) References Cited

FOREIGN PATENT DOCUMENTS

WO     WO-2011031935 A1 *  3/2011  ............. A61K 31/70

OTHER PUBLICATIONS

International Search Report and Written Opinion from PCT/US2022/033786 dated Nov. 16, 2022, 9 pgs.
Acurx Pharmaceuticals Inc., Acurx's Novel Lead Antibiotic Candidate Presented at Two Prominent International Scientific Conferences, Oct. 3, 2019, 4 pgs.
Acurx Pharmaceuticals to Present at Two Prominent International Healthcare Conferences, Nov. 4, 2019, 4 pgs.
Acurx Pharmaceuticals Inc., Advancing a Promising Antibacterial Against Clostridioides Difficile—advertisement feature in www.nature.com/biopharmdeal Oct. 18, 2021, 1 pg.
Acurx Announces Positive Phase 2A Clinical Trial Results for Ibezapolstat in C. difficile Infection at Prominent International Conference, Nov. 19, 2020, 4 pgs.
Acurx Successfully Completes Ph1 Clinical Trial for ACX-362E in CDI, Aug. 28, 2019, 4 pgs.
Acurx Announces First-In-Man Clinical Trial Data of ACX-362E for CDI, Feb. 27, 2019, 3 pgs.
Bassères, E. et al. Ibezapolstatis effective in vitro against high inoculum of Clostridium difficile, University of Houston College of Pharmacy, Houston, TX, Jul. 30, 2022, 1 pg.
Begum K., et al. In Vitro Activity of Omadacycline, a New Tetracycline Analog, and Comparators against Clostridioides difficile. Antimicrob Agents Chemother 2020; 64(8).
Britton R.A., et al. Role of the intestinal microbiota in resistance to colonization by C. difficile. Gastroenterology 2014; 146: 1547-53.
Cohen S. H. et al., Clinical Practice Guidelines for Clostridium difficile Infection in Adults: 2010 Update by the Society for Healthcare Epidemiology of America (SHEA) and the Infectious Diseases Society of America (IDSA), Infection Control and Hospital Epidemiology, vol. 31, No. 5, May 2010, pp. 431-455.
Davis M. L., et al. Multicentre derivation and validation of a simple predictive index for healthcare-associated C. difficile infection. Clin Microbiol Infect 2018; 24: 1190-4.
Dvoskin, S. et al., A Novel Agent Effective against Clostridium difficile infection, Antimicrob. Agents Chemother. 2012, 56(3):1624. DOI: 10.1128/AAC.06097-11, Published Ahead of Print Dec. 27, 2011, 4 pgs.
Fadrosh D. W., et al. An improved dual-indexing approach for multiplexed 16S rRNA gene sequencing on the Illumina MiSeq platform. Microbiome 2014; 2(1): 6.
Garey K. W., et al. A randomized, double-blind, placebo-controlled, single and multiple ascending dose Phase 1 study to determine the safety, pharmacokinetics and food and faecal microbiome effects of ibezapolstat administered orally to healthy subjects. J Antimicrob Chemother 2020;75(12):3635-3643. DOI: 10.1093/jac/dkaa364.
Garey, K. W., et al., A Randomized, Double-blind, Placebo-controlled, Single and Multiple Ascending Dose Phase 1 Study to Determine the Safety, Pharmacokinetics, Food, and Fecal Microbiome Effects of ACX-362E Administered Orally to Healthy Subjects, Oct. 2019, 13 pgs.
Garey, K. W., et al., DNA polymerase IIIC inhibitor ibezapolstat, first of a new class of antibiotics with a novel mechanism of action: Clinical Trial Update, Nov. 14, 2020, 1 pg.
Garey, K. W., C diff Foundation Late-Breaker: Ibezapolstat Clinical Update, Nov. 14, 2020; video at https://www.acurxpharma.com/news-media/videos/video/2906/video-presentation-of-clinical-data-by-dr-kevin-garey.
Slides presented in video listed in C18, Garey, K. W., C diff Foundation Late-Breaker: Ibezapolstat Clinical Update, Nov. 14, 2020, 18 pgs.
Unofficial Transcript of video listed in C18, Garey, K. W., C diff Foundation Late-Breaker: Ibezapolstat Clinical Update, Nov. 14, 2020, 5 pgs.
Gonzales-Luna A. J., et al. PCR ribotypes of Clostridioides difficile across Texas from 2011 to 2018 including emergence of ribotype 255. Emerg Microbes Infect 2020; 9(1): 341-7.
Gonzales-Luna A.J., et al., Systems biology evaluation of refractory Clostridioides difficile infection including multiple failures of fecal microbiota transplantation, Anaerobe 2021:102387. DOI: 10.1016/j.anaerobe.2021.102387.

(Continued)

*Primary Examiner* — Umamaheswari Ramachandran
(74) *Attorney, Agent, or Firm* — Crowell & Moring LLP

(57) ABSTRACT

The invention relates to methods of using ibezapolstat to increase the health of the gut microbiome. The invention provides methods of simultaneously treating *C. difficile* infections while at the same time reducing the likelihood of or preventing the recurrence of *C. difficile* infection. The invention also provides methods of increasing the health of the gut microbiome by increasing the number of Actinobacteria and/or Firmicutes in the gut.

13 Claims, 29 Drawing Sheets

(56) References Cited

OTHER PUBLICATIONS

Isaac S., et al., Short- and long-term effects of oral vancomycin on the human intestinal microbiota. J Antimicrob Chemother 2017; 72: 128-36.

Jangi and Lamont, Asymptomatic Colonization by Clostridium difficile in Infants: Implications for Disease in Later Life, JPGN, vol. 51, No. 1, Jul. 2010.

Kachrimanidou, Insights into the Role of Human Gut Microbiota in Clostridioides difficile Infection, Microorganisms 2020, 8, 200, doi:10.3390/microorganisms8020200.

Korthauer K., et al. A practical guide to methods controlling false discoveries in computational biology. Genome Biol 2019;20(1):118. DOI: 10.1186/s13059-019-1716-1.

Magill S. S., et al. Changes in prevalence of health care-associated infections in U.S. hospitals. N Engl J Med 2018; 379: 1732-44.

McDonald L. C., et al. Clinical practice guidelines for C. difficile infection in adults and children: 2017 update by the Infectious Diseases Society of America (IDSA) and Society for Healthcare Epidemiology of America (SHEA). Clin Infect Dis 2018; 66: 987-94.

Mueller, et al., The infant microbiome development: mom matters, Trends in Molecular Medicine, Feb. 2015, vol. 21, No. 2.

Mullish B. H, et al. The gut microbiome: what every gastroenterologist needs to know, Frontline Gastroenterology 2021;12:118-127.

Murray, B. et al. In vitro activity of the novel antibacterial agent Ibezapolstat (ACX-362E) against Clostridioides difficile. J Antimicrob Chemotherapy doi:10.1093/jac/dkaa134, Mar. 14, 2020, 7 pgs.

Murray, B. et al. Time-kill Kinetics of the Novel Antibacterial Agent ACX-362E against Clostridioides difficile, Micromyx, Kalamazoo, MI; Presentation #48 ASM-ESCMID, Sep. 5, 2019.

Peng Z., et al., Update on antimicrobial resistance in C. difficile: resistance mechanisms and antimicrobial susceptibility testing. J Clin Microbiol 2017; 55: 1998-2008.

Qian X. et al., Ridinilazole, a narrow spectrum antibiotic for treatment of Clostridioides difficile infection, enhances preservation of microbiota-dependent bile acids. Am J Physiol Gastrointest Liver Physiol 2020;319(2): G227-G237. DOI: 10.1152/ajpgi.00046.2020.

Ridlon J. M., et al. Bile salt biotransformations by human intestinal bacteria. J Lipid Res 2006; 47(2): 241-59.

Rizzatti, L. R. et al., Proteobacteria: A Common Factor in Human Diseases, BioMed Research International, vol. 2017, Article ID 9351507, 7 pages, 2017. https://doi.org/10.1155/2017/9351507.

Scherer M., et al. Rapid quantification of bile acids and their conjugates in serum by liquid chromatography-tandem mass spectrometry. J Chromatogr B Analyt Technol Biomed Life Sci 2009;877(30):3920-5. DOI: 10.1016/j.jchromb.2009.09.038.

Segata N., et al. Metagenomic biomarker discovery and explanation. Genome Biol 2011;12(6):R60. DOI: 10.1186/gb-2011-12-6-r60.

Stevens V.W. et al. Comparative effectiveness of vancomycin and metronidazole for the prevention of recurrence and death in patients with C. difficile infection. JAMA Intern Med 2017; 177: 546-53.

Walker J. N., et al. Insights into the Microbiome of Breast Implants and Periprosthetic Tissue in Breast Implant-Associated Anaplastic Large Cell Lymphoma. Sci Rep 2019; 9(1): 10393.

Xu, Wei-Chu, et al., Discovery and development of DNA polymerase IIIC inhibitors to treat Gram-positive infections., Bioorganic & Medicinal Chemistry, Aug. 2019, 9 pgs.

International Preliminary Report on Patentability (PCT/IB/326 & PCT/IB/373) issued in PCT Application No. PCT/US2022/033786 dated Dec. 28, 2023, including English translation of document C1 (Written Opinion (PCT/ISA/237), filed on Jan. 19, 2023) (6 pages).

* cited by examiner

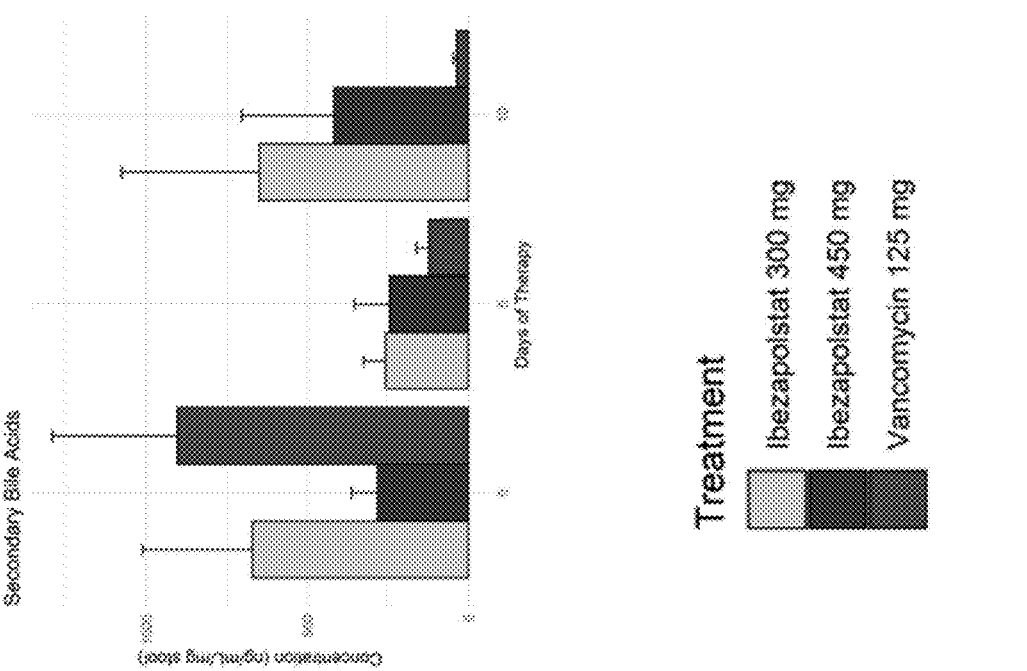
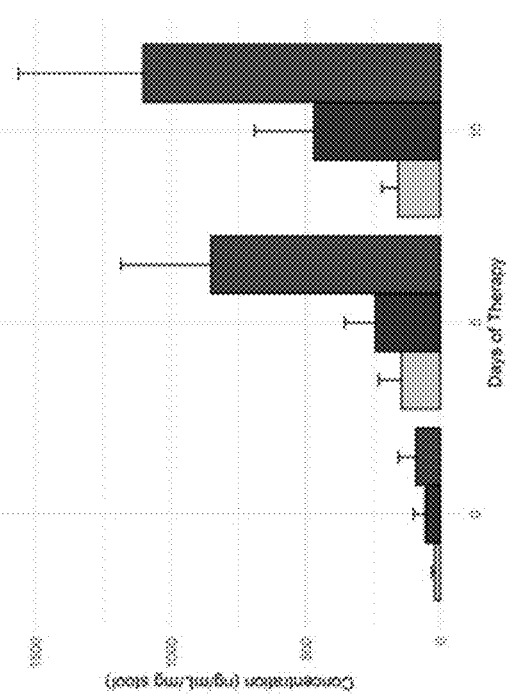
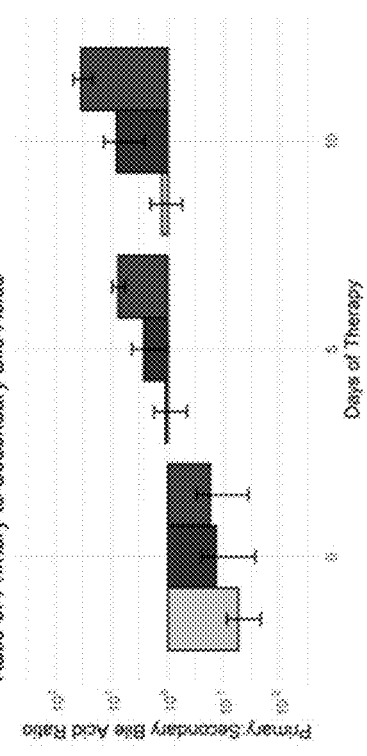

USE OF IBEZAPOLSTAT TO PROMOTE MICROBIOME HEALTH

All publications, patents and patent applications referred to herein are incorporated by reference in their entirety to the same extent as if each individual publication, patent or patent application was specifically and individually indicated to be incorporated by reference in its entirety.

The invention relates to methods of using ibezapolstat to increase the health of the gut microbiome. The invention provides methods of simultaneously treating *Clostridioides difficile* (*C. difficile*; formerly known as *Clostridium difficile*) infections (CDI) while at the same time reducing the likelihood of or preventing the recurrence of *C. difficile* infection. The invention also provides methods of increasing the health of the gut microbiome by increasing the number of Actinobacteria and/or Firmicutes in the gut.

BACKGROUND

The mucosal surfaces of the body contain complex and specialized microbial communities, often referred to as the microbiome or microbiota. (Mullish B H, et al. Frontline Gastroenterology 2021;12:118-127). The microbiota or microbiome of the human gastrointestinal tract is estimated to consist of up to 100 trillion microorganisms, most of them being found in the large intestine. (Kachrimanidou, Microorganisms 2020, 8, 200). While the gastrointestinal microbiome is diverse, in healthy adults it is predominantly composed of bacteria from two major phyla, Firmicutes (Gram-positive spore forming organisms) and Bacteroidetes (Gram-negative non-spore forming organisms). These two phyla typically comprise approximately 90% of the microbiome. (Mullish B H, et al. Frontline Gastroenterology 2021; 12:118-127).

In addition to Firmicutes and Bacteroidetes, the gut microbiome also is made up of Actinobacteria, Fusobacteria, Verrucomicrobia, and Proteobacteria. (Mullish). The Proteobacteria phylum is made up of Gram-negative facultative anaerobes and while some members of the Proteobacteria phylum are part of a healthy gut, this phylum also comprises the common Gram-negative pathobionts such as *Salmonella*, *Shigella*, and *Escherichia coli*. (Mullish). And an increasing amount of data indicates Proteobacteria as a possible microbial signature of disease. (Rizzatti, L. R. et al., "Proteobacteria: A Common Factor in Human Diseases", *BioMed Research International*, vol. 2017, Article ID 9351507, 7 pages, 2017. https://doi.org/10.1155/2017/9351507). Actinobacteria are present in large proportion in children and generally decrease in overall proportion with age (replaced by Firmicutes and Actinobacteria). At birth, facultative anaerobic species such as *E. coli, Staphylococcus*, and *Streptococcus* colonize the infant gut and produce anaerobic environs in the first few days of life that allow strict anaerobes like Bacteroides (Bacteroidetes phylum) and *Bifidobacterium* (Actinobacteria phylum) to thrive. (Mueller, et al., Trends in Molecular Medicine, February 2015, Vol. 21, No. 2). Over the first year of life, and through the exposure of the infants to the environment and either breast milk or formula, the gut microbiome evolves into the mature biome that approximates the adult gut microbiome. (Jangi and Lamont, JPGN, Vol. 51, No. 1, July 2010).

The gut microbiome is complex and has a mutually beneficial relationship with the host. Through this relationship, the microbiome provides a number of benefits to the host, including shaping the intestinal and systemic immune system, maintaining the healthy intestinal epithelium, harvesting energy from food and protection against pathogens. (Mullish). When the composition of the microbiome is altered from its normal diversity, these beneficial physiological functions are disrupted. This is called dysbiosis. (Mullish). When the gut microbiome is in a state of dysbiosis, the microbiome has fewer beneficial microbes (symbionts) and more of the potentially harmful microbes (pathobionts). (Mullish).

In addition to the benefits described in the preceding paragraph, the gut bacteria metabolize conjugated bile acids through the activity of two sets of enzymes. The first set, bile salt hydrolases (BSHs), remove the conjugated taurine or glycine to generate unconjugated bile acids. Once unconjugated, the primary bile acids can be further metabolized by the 7α-dehydroxylation pathway to produce secondary bile acids. There have been reports that the conjugated and unconjugated primary bile acids taurocholate (TCA) and cholate (CA), respectively, promote *C. difficile* spore germination, whereas secondary bile acids such as lithocholate (LCA) and deoxycholate (DCA) generally inhibit vegetative growth of *C. difficile*. (Qian et al., Am J Physiol Gastrointest Liver Physiol 319: G227-G237, 2020).

*Clostridioides difficile* infection (CDI) is the most common cause of healthcare-associated infections in the USA. (Magill S S, et al. Changes in prevalence of health care-associated infections in U.S. hospitals. N Engl J Med 2018; 379: 1732-44). *C. difficile* can sometimes be a normal component of the healthy gut microbiome, but when the microbiome is thrown out of balance, the *C. difficile* can thrive and cause disease (known as CDI). After colonization with *C. difficile*, the organism produces and releases the main virulence factors, the two large clostridial toxins A (TcdA) and B (TcdB). (Kachrimanidou, Microorganisms 2020, 8, 200; doi:10.3390/microorganisms8020200). TcdA and TcdB are exotoxins that bind to human intestinal epithelial cells and are responsible for inflammation, fluid and mucous secretion, as well as damage to the intestinal mucosa. *C. difficile* causes a wide spectrum of clinical symptoms ranging from mild diarrhea to severe life-threatening colonic perforation and toxic megacolon. CDI is predisposed to disruption of the host microbiome usually caused by prior use of high-risk antibiotics. (Davis M L, et al. Multicentre derivation and validation of a simple predictive index for healthcare-associated *C. difficile* infection. Clin Microbiol Infect 2018; 24: 1190-4). Through the treatment with broad spectrum antibiotics, for example, there can be an almost total loss of Bacteroidetes, a reduction in Firmicutes and an overgrowth of Proteobacteria; these changes allow the *C. difficile* spores to germinate and the colony can grow and become pathogenic. (Mullish). Once *C. difficile* is activated, its two toxins are produced in the colon that cause disease. (Britton R A, et al. Role of the intestinal microbiota in resistance to colonization by *C. difficile*. Gastroenterology 2014; 146: 1547-53).

Approximately 60% to 70% of healthy newborns and infants are colonized by *C. difficile*. (Jangi 2010). However, for reasons not yet fully understood, these colonized infants show no ill effects from the potent exotoxins released by this anaerobe, in contrast to older children and adults who are susceptible to severe diarrhea and colitis. The organism is acquired in infancy, as in adults, from environmental contamination in the nursery or home environment. The infant gut is frequently colonized by toxigenic strains of *C. difficile* with colony counts as high as those seen in adults with pseudomembranous colitis (which is a severe manifestation of CDI). (Jangi 2010). One possible reason for the asymptomatic colonization in infants could be the presence and competition of other commensal flora, such as *Bifidobacterium* (in the Actinobacteria phylum) and *Lactobacillus* (in the Firmicutes phylum). (Jangi 2010). In fact, as reported in Jangi, both *Bifidobacterium* and *Lactobacillus* were able to inhibit the growth of specific *C. difficile* strains.

Antimicrobial therapy is the hallmark of CDI treatment, although there are limited treatment options. Historically, metronidazole was widely used for the treatment of CDI but it is no longer recommended due to unacceptably high failure rates compared with vancomycin, higher mortality and cumulative toxicity. (McDonald L C, et al. Clinical practice guidelines for *C. difficile* infection in adults and children: 2017 update by the Infectious Diseases Society of America (IDSA) and Society for Healthcare Epidemiology of America (SHEA). Clin Infect Dis 2018; 66: 987-94; and Stevens V W, et al. Comparative effectiveness of vancomycin and metronidazole for the prevention of recurrence and death in patients with *C. difficile* infection. JAMA Intern Med 2017; 177: 546-53).

Currently, either vancomycin or fidaxomicin are the recommended antibiotics for CDI for their ability to kill *C. difficile* and for resolving clinical symptoms. (Gonzales-Luna A J, et al., Systems biology evaluation of refractory *Clostridioides difficile* infection including multiple failures of fecal microbiota transplantation, Anaerobe, https://doi.org/10.1016/j.anaerobe.2021.102387). While vancomycin is recommended by the IDSA treatment guidelines, it is associated with a high rate of CDI recurrence and has recently been shown to have increased resistance due to profound disruption of the host microbiota. (Isaac S, et al., Short- and long-term effects of oral vancomycin on the human intestinal microbiota. J Antimicrob Chemother 2017; 72: 128-36; and Peng Z, et al., Update on antimicrobial resistance in *C. difficile*: resistance mechanisms and antimicrobial susceptibility testing. J Clin Microbiol 2017; 55: 1998-2008). Treatment with vancomycin results in decreased microbiome diversity of Firmicutes, Actinobacteria and Bacteroidetes with a characteristic Proteobacteria overgrowth. (Garey 2020). Proteobacteria overgrowth is associated with a markedly increased risk of systemic infections with multi-drug resistant (MDR) Gram-negative organisms. Vancomycin is associated with high rates of CDI recurrence—with approximately 20-25% of patients having a recurring infection after treatment is discontinued. (Gonzales-Luna).

Fidaxomicin has a narrower spectrum of activity than vancomycin and causes less dysbiosis over the course of treatment. Unlike vancomycin, fidaxomicin binds to *C. difficile* spores preventing outgrowth of vegetative cells thereby resulting in recurrence rates that are approximately 50% lower than other treatments. (Gonzales-Luna). While fidaxomicin has a lower recurrence rate there are reports that resistance has manifested via mutations in the rpoB gene. (Garey 2020). Regardless of chosen therapy, the CDI recurrence rate increases with each subsequent episode of CDI, often requiring prolonged courses of antibiotics to control the disease.

Further, there have been reports that broad-spectrum antibiotic treatment leads to a loss in secondary bile acids. (Qian). Additionally, there have been reports that patients suffering from *C. difficile* recurrent infections have higher primary bile acids, whereas heathy subjects have higher secondary bile acids. (Qian). These results suggest that a treatment that results in more secondary bile acids may be effective in preventing recurrent CDI.

Thus, new therapies with distinct mechanisms of actions directed against *C. difficile* are urgently needed. In fact, the CDC lists *C. difficile* in the "urgent" category of priority pathogens where new classes of antibiotics are needed. In particular, there is a need for a CDI treatment that also provides an environment for the microbiome to resist recurrence without any further treatment necessary. There is also a need for a CDI treatment that promotes microbiome health.

SUMMARY OF THE INVENTION

The present invention provides a method of simultaneously treating a *C. difficile* infection and reducing the likelihood of or preventing the recurrence of *C. difficile* infection in a subject comprising administering an effective amount of ibezapolstat to a subject suffering from a *C. difficile* infection, wherein the administration of the effective amount of ibezapolstat simultaneously treats the *C. difficile* infection and reduces the likelihood or prevents recurrence of *C. difficile* infection within 90 days. The administration of ibezapolstat may be continued until a clinical cure of the *C. difficile* infection is achieved or terminated when a clinical cure of the *C. difficile* infection is achieved. The administration of the effective amount of ibezapolstat may reduce the likelihood or prevents recurrence of *C. difficile* infection within 30 days.

The present invention also provides a method of promoting the growth of Actinobacteria in a subject suffering from a *C. difficile* infection comprising administering an effective amount of ibezapolstat to treat or prevent said *C. difficile* infection, wherein the amount of Actinobacteria in the subject's gut microbiome is increased or the proportion of Actinobacteria compared to Proteobacteria is increased. The administration of ibezapolstat may be continued until a clinical cure of the *C. difficile* infection is achieved or terminated when a clinical cure of the *C. difficile* infection is achieved.

The present invention further provides a method of improving the health of a gut microbiome comprising administering an effective amount of ibezapolstat to a subject suffering from a *C. difficile* infection wherein the proportions of phyla of bacteria in the subject's gut microbiome are adjusted to a healthier balance compared to the subject's gut microbiome prior to the administration of the ibezapolstat.

The present invention further provides a method of increasing the amount of Actinobacteria in a gut microbiome comprising administering an effective amount of ibezapolstat to a subject in need thereof wherein the amount of Actinobacteria is higher in the gut microbiome compared to amount of Actinobacteria in the gut microbiome prior to the administration of the ibezapolstat.

The present invention further provides a method of improving the health of a gut microbiome comprising administering an effective amount of ibezapolstat to a subject in need thereof wherein the proportions of phyla of bacteria in the subject's gut microbiome are adjusted to a healthier balance compared to the subject's gut microbiome prior to the administration of the ibezapolstat.

BRIEF DESCRIPTION OF THE DRAWINGS

Each box represents one patient given a 10-day course of study drug or placebo with a 13-day study period

FIG. 7 shows summary changes of primary (7A) and secondary (7B) as well as the ratio of primary: secondary bile acids (7C) over time. Values represent mean±standard error.

DESCRIPTION OF THE INVENTION

Figure 1:
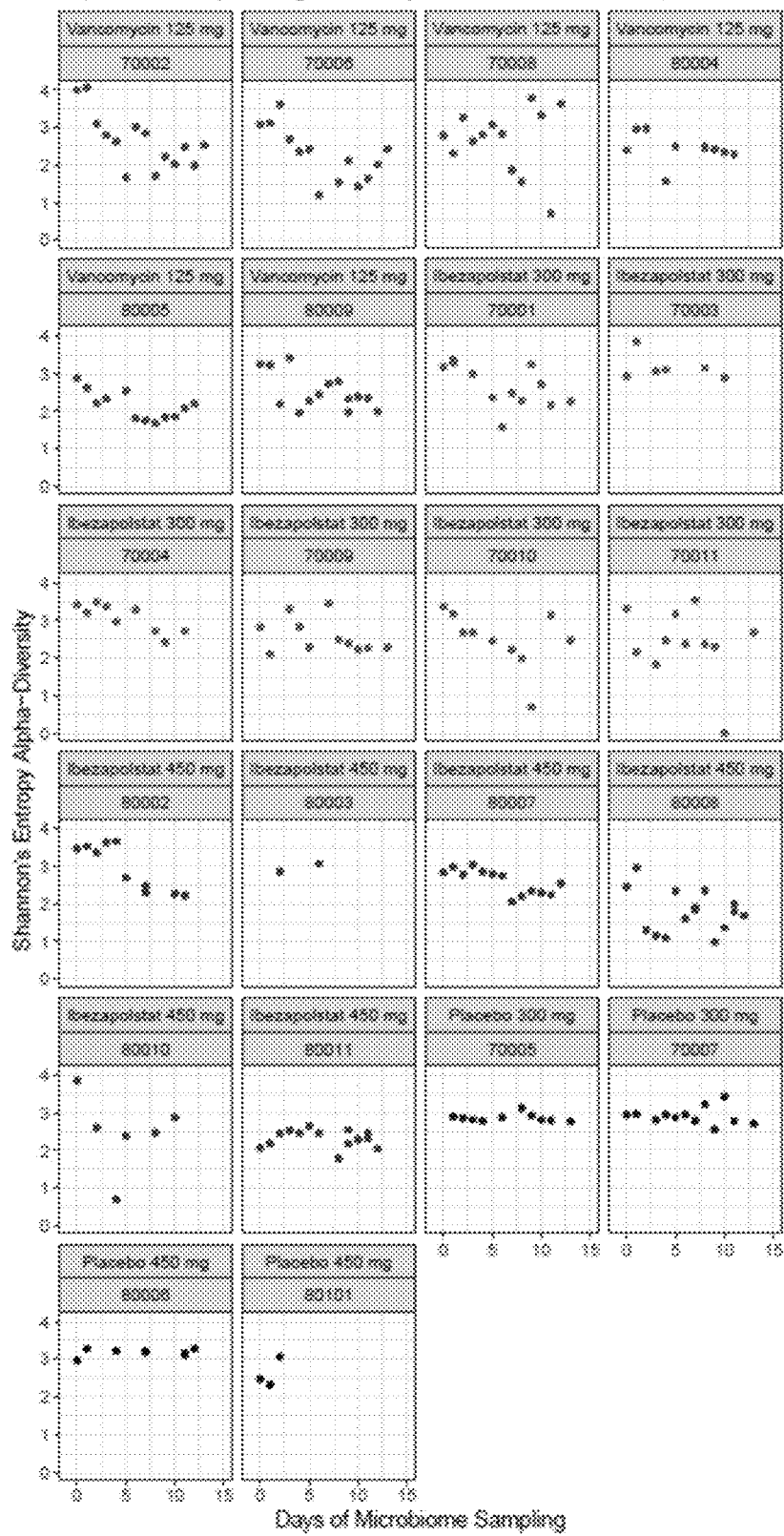
FIG. 1 shows the alpha diversity of species in the microbiome did not significantly decrease upon administration of ibezapolstat (ACX362E) as determined using Shannon's index. In contrast, the diversity of bacterial species decreased upon administration of 125 mg of vancomycin. The subjects labeled placebo are those with a healthy gut where no ibezapolstat or vancomycin was administered.

Described herein are methods of using ibezapolstat to increase the health of the gut microbiome. The invention provides methods of treating *C. difficile* infections while at the same time reducing the likelihood of or preventing the recurrence of *C. difficile* infection. The invention also provides methods of increasing the health of the gut microbiome by increasing the number of Actinobacteria in the gut and/or increasing the proportion of Actinobacteria relative to the other phyla of bacteria in the microbiome.

By "*C. difficile* infection" or "CDI" is meant the invasion of a host animal, e.g., a mammal, by *C. difficile*. For example, the infection may include the excessive growth of *C. difficile* that is normally present in or on the body of a mammal or growth of *C. difficile* that is not normally present in or on the mammal. More generally, a *C. difficile* infection can be any situation in which the presence of the *C. difficile* or the toxins released by *C. difficile*, is damaging to a host animal. An animal is "suffering" from a *C. difficile* infection when an excessive amount of *C. difficile* is present in or on the animal's body, or when the presence of *C. difficile* toxins is damaging the intestinal cells or other tissue of the animal. In one embodiment, the number of a particular genus or species of *C. difficile* is at least 2, 4, 6, or 8 logs higher than the number found in a healthy microbiome. Alternatively, the number of *C. difficile* could be the same as in a healthy microbiome but is producing toxins. Presence of a *C. difficile* infection may be characterized by the presence of toxin in the stools, usually by testing for the gene that produces toxin B, using a PCR method or using an ELISA assay able to detect toxin proteins.

By "effective amount" is meant an amount sufficient to effect beneficial or desired clinical or biochemical results. An effective amount can be administered one or more times. For purposes of this invention, an effective amount is the amount of ibezapolstat which when administered to a site of infection or potential infection will treat or prevent a *C. difficile* infection, while simultaneously increasing the amount and/or proportion of Actinobacteria and/or Firmicutes in the microbiome.

By "administration" or "administering" is meant a method of giving one or more unit doses of ibezapolstat to an animal, e.g., a mammal (such as topical, oral, intravenous, intraperitoneal, or intramuscular administration). The method of administration may vary depending on various factors, e.g., the components of the pharmaceutical composition, site of the potential or actual infection, and severity of the actual microbial infection.

By "inhibiting" is meant reducing the cellular growth rate of the *C. difficile* bacterium by at least 80%. In certain embodiments, the growth can be inhibited by 90%, 95%, or even 99% or more. The degree of inhibition can be ascertained, for example, by an in vitro growth assay, e.g., by a standard liquid culture technique. Inhibition of colony formation at suitable MICs (minimal inhibitory concentrations), e.g., <100 µg/ml, more preferably <10 µg/ml, are preferred.

By "treatment" is meant an approach for obtaining beneficial or desired clinical results. For the purposes of this invention, beneficial or desired clinical results include, but are not limited to, alleviation of symptoms, diminishment of extent of disease, stabilization (i.e., not worsening) of a state of disease, delay or slowing of disease progression, amelioration or palliation of the disease state, and remission (whether partial or total), whether detectable or undetectable. "Treatment" refers to both therapeutic treatment and prophylactic or preventative measures. Those in need of treatment include those already with the disorder as well as those in which the disorder is to be prevented and/or recurrence is to be prevented. "Palliating" a disease means that the extent and/or undesirable clinical manifestations of a disease state are lessened and/or the time course of the progression is slowed or lengthened, as compared to a situation without treatment.

By "microbiome" is meant the microorganisms in a particular environment (including the body or a part of the body). Preferably, the microbiome is located in the gut.

A "healthy microbiome" could be described in terms of ecologic stability (i.e., ability to resist community structure change under stress or to rapidly return to baseline following a stress-related change), by an idealized (presumably health-associated) composition or by a desirable functional profile (including metabolic and trophic provisions to the host). A healthy adult microbiome may also be characterized by a majority of bacterial species in the Firmicute or Bacteroidetes phylum and a minority in the Actinobacteria and Proteobacteria phylum. A healthy newborn microbiome may be characterized by a majority of bacterial species in the Bacteroidetes and Actinobacteria phylum.

By "improving the health of a gut microbiome" is meant that the composition of the microbiome is brought to a majority proportion of bacterial species from the Actinobacteria, Firmicute or Bacteroidetes phylum with a minority of Proteobacteria phylum. Alternatively, improving the health of a gut microbiome can mean increasing the proportion of bacterial species in the Actinobacteria phylum, such as is present in a healthy newborn gut microbiome. A subject may be suffering from a C. difficile infection or not suffering from a C. difficile infection.

By "reducing the likelihood of C. difficile infection" is meant prophylactic treatment or treatment resulting in a reduction (e.g., at least 5%, 10%, 15%, 20%, 25%, 30%, 35%, 40%, 50%, 60%, 70%, 80%, 90%, or 95%) for a subject or a patient population in the chance or rate of developing a C. difficile infection by administering ibezapolstat compared to a subject or patient population not receiving ibezapolstat.

By "clinical cure" is meant the initial infection has cleared. It is preferably measured about 10-12 days after diagnosis after a subject has received a treatment course.

By "sustained clinical cure" is mean the subject had a clinical cure and the infection did not recur. It is measured at day 30-90 days after diagnosis.

By "recurrence" is meant that the subject had a clinical cure and the infection occurred again within 30-90 days' time.

The microbiome of the healthy gut is composed of major bacterial groups called phyla. Firmicutes (Gram-positive spore forming organisms) and Bacteroidetes (Gram-negative non-spore forming organism) are most common and together generally comprise greater than 90% of the healthy adult gut microbiome. The adult gut microbiome also contains Actinobacteria, Fusobacteria, Verrucomicrobia, and Proteobacteria. Actinobacteria are present in large proportion in children and generally decrease in overall proportion with age (replaced by Firmicutes and Actinobacteria). Proteobacteria (Gram-negative facultative anaerobes) generally comprise 2-5% of the healthy microbiome. When the composition of the microbiome is altered from its normal diversity, the normal physiological functions are disrupted—called dysbiosis. Patients suffering from C. difficile infection are in a state of dysbiosis. The dysbiosis associated with subjects with C. difficile infection includes an increased proportion of Proteobacteria (often referred to as a "bloom") and a reduced number of Firmicutes and Bacteroidetes Ibezapolstat is 2-((3,4-dichlorobenzyl)amino)-7-(2-morpholinoethyl)-1,7-dihydro-6H-purin-6-one. Procedures for the synthesis of 1,7-dihydro-6H-purin-6-one compounds and their use in inhibiting bacterial growth are disclosed in U.S. Pat. Nos. 6,926,763 and 8,796,292 incorporated by reference herein. Ibezapolstat is a DNA polymerase IIIC inhibitor. It has an anti-Gram-positive spectrum of antibacterial activity useful in the treatment of C. difficile infections. Ibezapolstat's mechanism of action targets low G+C (fewer G and C DNA bases than A and T bases) content Gram-positive bacteria, primarily Firmicutes including C. difficile. The DNA polymerase IIIC enzyme is essential for replication of low G+C content Gram-positive bacteria and thus is selective for Firmicutes such as C. difficile yet inactive against other host microbiota such as Actinobacteria or Bacteroidetes.

The administration of ibezapolstat results in a distinctly different microbiome profile compared to the administration of vancomycin, the current recommended treatment for C. difficile infection. For example, a larger proportion of desirable Actinobacteria and Firmicute phyla were seen in ibezapolstat-treated subjects compared with a larger number and proportion of undesirable Proteobacteria in vancomycin-treated subjects. Proteobacterial over-growth is associated with a markedly increased risk of systemic infections with MDR Gram-negative organisms. Thus, not only does ibezapolstat not harm the population of desirable Actinobacteria and Firmicutes in contrast to vancomycin, but ibezapolstat unexpectedly increases the number and/or proportion of Actinobacteria and Firmicutes present in the microbiome. See FIGS. 3 and 4. By promoting the growth of healthy bacteria, such as Actinobacteria and Firmicutes, and by not causing an increase in Proteobacteria, ibezapolstat also provides a microbiome that prevents or reduces the likelihood of recurrence of C. difficile infection.

Ibezapolstat may be formulated into pharmaceutical compositions for administration to human or animal subjects in a biologically compatible form suitable for administration in vivo or in vitro. Accordingly, the present invention provides a pharmaceutical composition including a compound of the invention in admixture with an excipient.

The present invention provides methods of simultaneously treating a C. difficile infection and reducing the likelihood of or preventing the recurrence of C. dfficile infection in a subject by administering an effective amount of ibezapolstat to a subject suffering from a C. difficile infection. The administration of the effective amount of ibezapolstat simultaneously treats the C. difficile infection and reduces the likelihood or prevents recurrence of C. difficile infection within 30-90 days. Preferably, the administration of ibezapolstat may be continued until the C.

*difficile* infection is clinically cured. Preferably, the administration of ibezapolstat may be terminated once a clinical cure is achieved.

The present invention further provides methods of promoting the growth of Actinobacteria in a subject suffering from a *C. difficile* infection comprising administering an effective amount of ibezapolstat to treat or prevent the *C. difficile* infection. The amount of Actinobacteria in the subject's gut microbiome is increased or the proportion of Actinobacteria is increased. The administration of ibezapolstat is continued until a clinical cure of the *C. difficile* infection is achieved. Preferably, the administration of ibezapolstat is terminated when a clinical cure of the *C. difficile* is achieved. The percentage of Actinobacteria following the administration of ibezapolstat may increase by at least 5%, 10%, 15%, 20%, 25%, 30%, 35%, 40%, 50%, 60%, 70%, 80%, 90%, or 95%.

The present invention further provides a method of improving the health of a gut microbiome comprising administering an effective amount of ibezapolstat to a subject suffering from a *C. difficile* infection. The proportions of phyla of bacteria in the subject's gut microbiome are adjusted to a healthier balance compared to the subject's gut microbiome prior to the administration of the ibezapolstat. For example, the percentage of Actinobacteria may increase by at least 5%, 10%, 15%, 20%, 25%, 30%, 35%, 40%, 50%, 60%, 70%, 80%, 90%, or 95%.

The present invention also provides a method of increasing the amount of Actinobacteria in a gut microbiome comprising administering an effective amount of ibezapolstat to a subject in need thereof wherein the amount of Actinobacteria is higher in the gut microbiome compared to amount of Actinobacteria in the gut microbiome prior to the administration of the ibezapolstat. The subject does not need to be suffering from a *C. difficile* infection. The present invention also provides a method of improving the health of a gut microbiome comprising administering an effective amount of ibezapolstat to a subject in need thereof, wherein the proportions of phyla of bacteria in the subject's gut microbiome are adjusted to a healthier balance compared to the person's gut microbiome prior to the administration of the ibezapolstat. The subject does not need to be suffering from a *C. difficile* infection.

Figure 2:
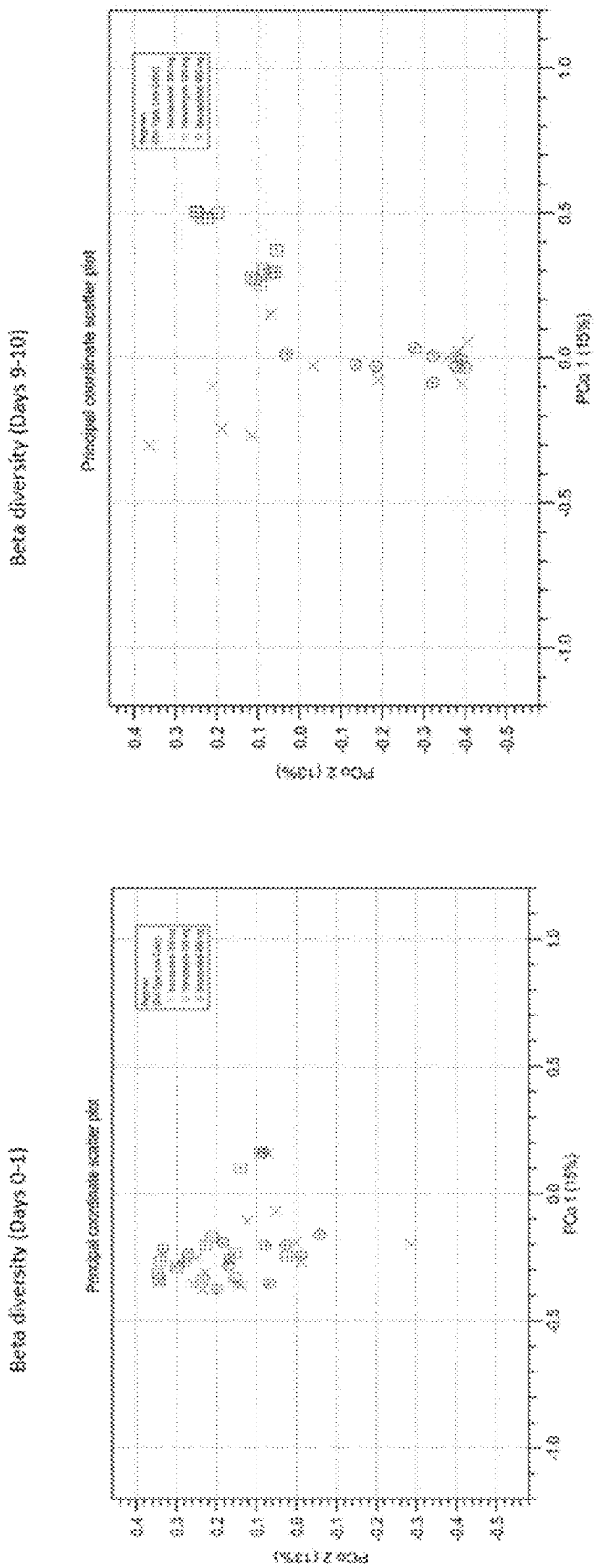
FIG. 2 shows the effect on the microbiome profile resulting from the administration of 300 mg and 450 mg ibezapolstat and from 125 mg vancomycin. The data is provided via PCoA Bray Curtis Plots. As can be seen in the figures, distinct ibezapolstat microbiome profiles were identified after 10 days of dosing compared to vancomycin.

As shown in FIG. 1, the diversity of bacterial species in the microbiome did not significantly decrease upon administration of ibezapolstat. In contrast, the diversity of bacterial species decreased upon administration of vancomycin. The subjects labeled placebo are those with a healthy gut where no ibezapolstat or vancomycin was administered. When compared with placebo, the administration of ibezapolstat did not significantly decrease diversity of the microbiome. Lower bacterial diversity is undesirable as it predicts recurrence of *C. difficile* infection over time. As shown in FIG. 2, the microbiome profile resulting from the administration of 300 mg and 450 mg ibezapolstat was distinct from the microbiome profile resulting from 125 mg vancomycin over the course of 10 days.

Figure 3:
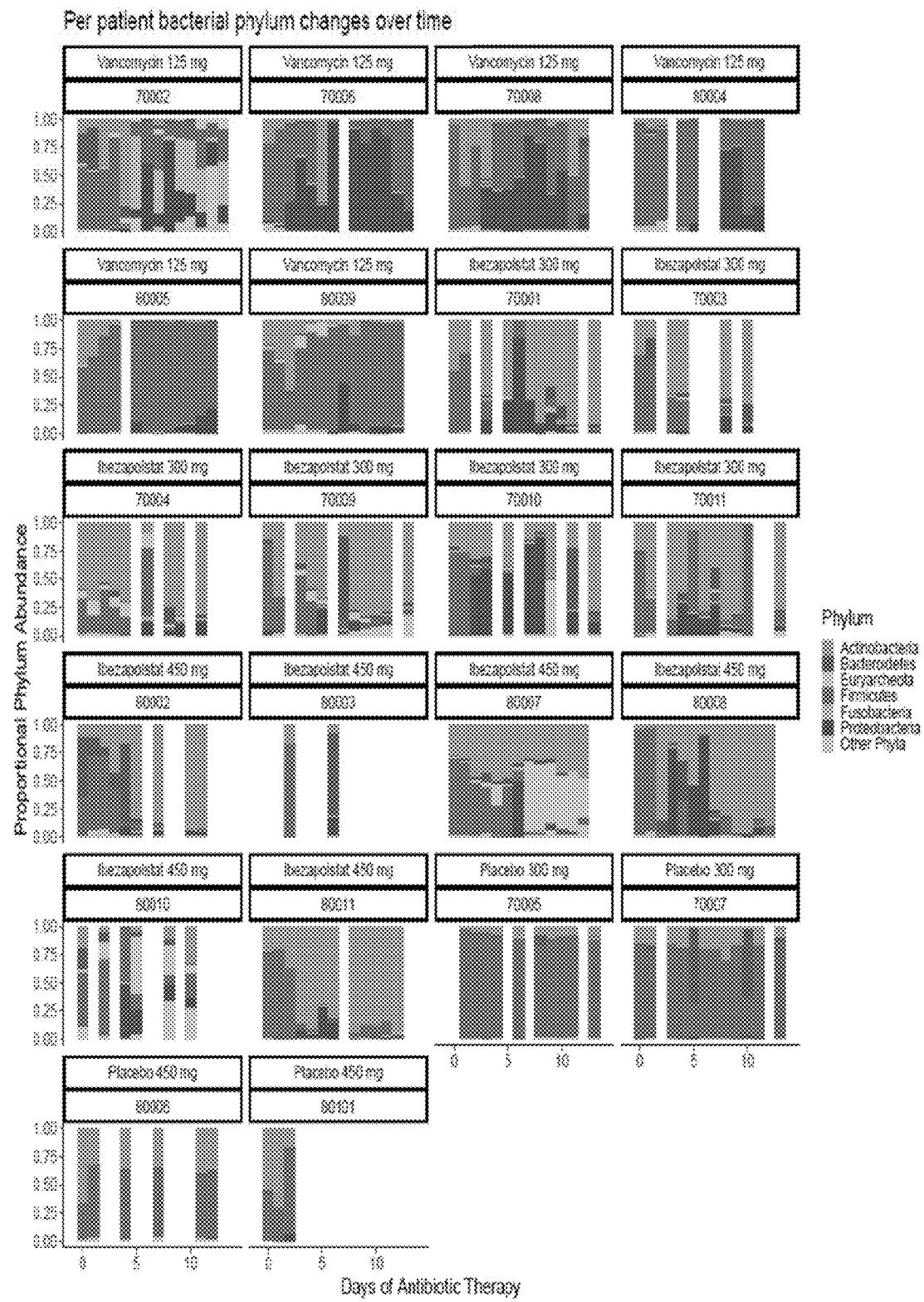
FIG. 3 shows the composition of the microbiome by bacterial phyla upon administration of 125 mg of vancomycin, 300 mg of ibezapolstat, and 450 mg of ibezapolstat. The subjects labeled placebo are those with a healthy gut where no ibezapolstat or vancomycin was administered. Each box represents one patient given a 10-day course of study drug or placebo with a 13-day study period

As shown in FIG. 3, upon administration of vancomycin there is an increase in Proteobacteria, which decreases the health and balance of the microbiome and increases the chance of recurrence of *C. difficile* infection. In contrast, administration of 300 mg of ibezapolstat resulted in an increase of Actinobacteria in the microbiome compared to other bacterial phyla. Administration of 450 mg of ibezapolstat also resulted in an increase of Actinobacteria compared to other bacterial phyla. Administration of ibezapolstat at either dose did not result in an increase of Proteobacteria seen upon administration of vancomycin.

Upon birth, children immediately begin to develop their gut microbiome by exposure to various species of bacteria. During early infancy, facultative anaerobic species such as *E. coli*, *Staphylococcus*, and *Streptococcus* colonize the infant gut and produce anaerobic environs in the first few days of life that allow strict anaerobes like Bacteroides (Bacterioidetes phylum) and *Bifidobacterium* (Actinobacteria phylum) to thrive. Also, approximately 60% to 70% of healthy newborns and infants are colonized by *C. difficile*—frequently with colonization counts as high as symptomatic adults suffering from CDI. These infants do not typically experience any symptoms from this colonization. The methods of the invention result in a gut microbiome closely resembling the healthy early infant gut microbiome, with high amounts of Actinobacteria. *Bifidobacterium*, a group of bacteria in the Actinobacteria phylum, inhibit the growth of *C. difficile* strains. Thus, the methods according to this invention result in a gut microbiome that will prevent or reducing the likelihood of recurrence of CDI.

Ibezapolstat fulfills three key criteria for an ideal anti-*C. difficile* antibiotic: ibezapolstat achieves high colonic concentrations with minimal systemic absorption; it has potent activity against *C. difficile* while, in contrast to oral vancomycin, causes minimal disruption of the gut microbiome; and it shows a potentially beneficial effect on gut bile acid metabolism.

In accordance with the methods of the invention, ibezapolstat may be administered to a subject or patient in a variety of forms depending on the selected route of administration, as will be understood by those skilled in the art. For human or animal use, ibezapolstat be administered by the oral, buccal, rectal and vaginal routes, or by topical administration, and the pharmaceutical compositions formulated accordingly. Preferably, the ibezapolstat is administered in an oral dosage form. Without limitation, for oral administration, the composition can be, for example, in the form of tablets, capsules, granules, liquid solutions and suspensions. The composition may also be administered via suppository or enema.

Ibezapolstat may be administered to an animal, preferably a human, alone or in combination with pharmaceutically acceptable excipients, as noted above, the proportion of which is determined by the solubility and chemical nature of the compound, chosen route of administration, and standard pharmaceutical practice. Ibezapolstat may be administered to adults or to children. The dosage of the compounds of the invention, and/or compositions comprising a compound of the invention, can vary depending on many factors, such as the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, the compounds of the invention can be provided in an aqueous physiological buffer solution containing about 0.1 to 10% w/v compound or in a solid dosage form such as a tablet or capsule. General dose ranges are from about 0.01 mg/kg to about 1 g/kg of body weight per day. Oral dosages of ibezapolstat may include amounts from about 10 mg to 1000 mg per day, preferably 100 mg to 900 mg per day, and more preferably at about 150, 300, 600, or 900 mg per day.

EXAMPLES

The foregoing description and examples have been set forth merely to illustrate the invention and are not meant to be limiting. Since modifications of the described embodiments incorporating the spirit and the substance of the invention may occur to persons skilled in the art, the invention should be construed broadly to include all variations within the scope of the claims and equivalents thereof.

Example 1

Microbiome Studies for the Phase I Healthy Volunteer Study:

Background: The microbiome of the healthy gut is composed of two major bacterial groups called phyla. Firmicutes (Gram-positive spore forming organisms) and Bacteroidetes (Gram-negative non-spore forming organism) are most common. A third phylum, Proteobacteria (Gram-negative facultative anaerobes), is present in low abundance but generally comprise 2-5% of the healthy microbiome. A fourth phylum, Actinobacteria is present in large proportion in children and generally goes down on overall proportion with age (replaced by Firmicutes and Actinobacteria). Patients suffering from C. difficile infection are in a state of dysbiosis, and often have an increased proportion of Proteobacteria, for example an overabundance of Proteobacteria or "Proteobacteria bloom", and a reduced number of Firmicutes and Bacteroidetes.

Ibezapolstat studies: Using stool samples from the phase I healthy volunteer study and shotgun metagenomic sequencing, it was demonstrated that treatment with ibezapolstat over 10 days results in a significantly different microbiome profile in subjects compared to subjects receiving vancomycin. The difference was a larger proportion of Actinobacteria and Firmicute Phylum in ibezapolstat treated subjects vs. a larger proportion of Proteobacteria in vancomycin treated subjects.

Methods and Materials

Materials: Standards for primary bile acids cholate (CA) and chenodeoxycholate (CDCA), conjugated primary bile acids glycocholate (GCA), taurocholate (TCA), glycochenodeoxycholate (GCDCA), and taurochenodeoxycholate (TCDCA), secondary bile acids lithocholate (LCA), deoxycholate (DCA), ursodeoxycholate (UDCA), and hyodeoxycholate (HDCA), and conjugated secondary bile acids glycolithocholate (GLCA), taurolithocholate (TLCA), glycodeoxycholate (GDCA), and taurodeoxycholate (TDCA) were purchased from Sigma.

Description of clinical trial: Twenty-two subjects (female: 33%) aged 30±8 years were enrolled. Six patients each were given either vancomycin, ibezapolstat 300 mg, or ibezapolstat 450 mg and an additional four were given placebo. Stool samples were collected daily as part of a recent phase I, healthy volunteer study of ascending dose ibezapolstat (300 or 450 mg given twice daily) with a vancomycin comparator arm given 125 mg four times daily and placebo, as described. (Garey K W, et al. A randomized, double-blind, placebo-controlled, single and multiple ascending dose Phase 1 study to determine the safety, pharmacokinetics and food and faecal microbiome effects of ibezapolstat administered orally to healthy subjects. J Antimicrob Chemother 2020; 75(12):3635-3643. DOI: 10.1093/jac/dkaa364.) Institutional review board approval was obtained (Midlands Institutional Review Board IRB #222220170383) and all volunteers signed an informed consent form prior to performing any study procedures. For this analysis, stool samples were collected daily for days 0 (baseline)-13 and day 30 follow-up if available from subjects given ibezapolstat 300 or 450 mg twice daily, vancomycin 125 mg given four time daily, or placebo for 10 days. Stool samples were immediately frozen at −80 C prior to shipping to the University of Houston on dry ice for analysis.

Stool DNA extraction and Shotgun Metagenomic Sequencing: Stool DNA was extracted using a DNAeasy Power Soil Pro kit (Qiagen, catalog number 1288-100) in a QiaCube automated DNA extraction system as previously described. (Garey K W, et al., J Antimicrob Chemother 2020; 75(12):3635-3643. DOI: 10.1093/j ac/dkaa364.) Shotgun metagenomic sequencing was carried out at the University of Houston Sequencing and Gene Editing Core (Houston, TX USA) using the Nextera DNA Flex Library Prep Kit for DNA library preparation and an Illumina NextSeq 500 platform for sequencing. CLC Genomic Workbench version 12 (Qiagen) was used for metagenomic assembly and creation of the abundance table.

Extraction of bile acids from stool samples: Stool samples were aliquoted and weighed (ranging from ~10 to ~150 mg), each aliquot was mixed well with 1 ml of 100% methanol containing the internal standards (LCA-d5, and CA-d5, 200 µg/L) by vortexing and ultrasonication. The mixture was placed overnight at 4° C. and centrifuged for 3 min at 10,000 g, the supernatant was transferred into a new tube and diluted by 10 folds with the pure water. Subsequently, the diluted supernatant was applied to the pre-conditioned Sep-Pak C18 Classic Cartridge or Waters Corp Oasis HLB 96-well Plate (Waters, USA). After being washed with 5% methanol, the bile-acid fraction was eluted with 100% methanol. The elution was dried under nitrogen, re-suspended in 2 ml of methanol/water (1:1, vol/vol), and stored at −20° C. until further analysis.

Bile acid analysis: Bile acids were quantified using targeted liquid chromatography mass spectrometry (LC-MS) analysis performed on a QTRAP 5500 mass spectrometer (Sciex, Framingham, MA, USA) adapted from a previously described method. (Scherer M, et al. Rapid quantification of bile acids and their conjugates in serum by liquid chromatography-tandem mass spectrometry. J Chromatogr B Analyt Technol Biomed Life Sci 2009; 877(30):3920-5. DOI: 10.1016/j.jchromb.2009.09.038.) Briefly, chromatographic separation between bile acids of similar mass and chemical structure was conducted on a C18 column (Phenomenex, Torrance, CA, USA) and with a gradient method using two mobile phases (Solvent A: methanol-water (1:1, vol/vol) with 10 mM ammonium acetate and 0.1% (wt/vol) ammonium hydroxide (pH 9); Solvent B: methanol with 10 mM ammonium acetate and 0.1% (wt/vol) ammonium hydroxide (pH 9). Quantification of each type of bile acid was calculated from the standard curves generated using unlabeled and stable isotope-labeled standards of bile acids. Bile acid concentrations were normalized by the corresponding sample weight.

Statistical Analysis

Subject specific and summary changes in bacterial taxa and alpha diversity was generated using R software. Linear regression models were built to assess proportional taxa differences at the Phylum, Class, Order, and Family level over time for subjects given vancomycin or ibezapolstat normalizing to taxa present in at least five percent of total samples. Linear regression models were also built to assess daily changes in alpha diversity measures (Shannon's, Simpson, and Pielous) over time for subjects given vancomycin or ibezapolstat. The Linear Effect Size algorithm (LEfSe) algorithm was used to visualize and identify significant differences in microbiota composition between baseline and day 10 samples. (Segata N, et al. Metagenomic biomarker discovery and explanation. Genome Biol 2011; 12(6):R60. DOI: 10.1186/gb-2011-12-6-r60.) Linear regression models were built to assess primary and secondary bile acid changes over time and the ratio of primary:secondary bile acids over time from subjects given vancomycin or ibezapolstat. All linear regression models used placebo results as baseline values and controlled for subject age, weight, and sex. SAS Vers 9.4 (Sas Institute, Cary NC) or R were used for all statistical analyses. To account for multiple analyses per aim, a reduced p value of $p<0.005$ was considered statistically significant unless otherwise stated to limit the false detection rate. (Korthauer K, et al. A practical guide to methods controlling false discoveries in computational biology. Genome Biol 2019; 20(1):118. DOI: 10.1186/s13059-019-1716-1.)

Alpha and Beta Diversity

Alpha and Beta Diversity: Alpha diversity tests for the diversity of bacterial species within a sample while beta diversity tests for differences in diversity between samples. Alpha and beta diversity of samples from healthy subjects given ibezapolstat was assessed compared to subjects given vancomycin using the methods described in Gonzales-Luna (Systems biology evaluation of refractory Clostridioides difficile infection including multiple failures of fecal microbiota transplantation. Anaerobe 2021:102387. DOI: 10.1016/j.anaerobe.2021.102387).

16S ribosomal RNA (rRNA) gene sequencing: 16S rRNA sequencing was performed to characterize microbial taxonomy as described in Gonzales-Luna 2021. The V3-V4 region of the 16S rRNA gene was sequenced using an Illumina-based sequencing platform with a minimum of 15,000 reads per sample to assess the gut microbiome community structure. Quality filtered sequence reads with at least 97% similarity were clustered into Operational Taxonomic Units (OTUs) and representative sequences from each OTU were assigned a taxonomic identity at the species level by searching against the NCBI 16S rRNA sequence database (release date Sep. 1, 2018) using NCBI BLAST+ package v2.8.1 2018. The microbial diversity indices were calculated using QIIME v1.9.0, where species richness and phylogenetic distance represented α-diversity, and Bray-Curtis and Weighted Unifrac were representative of β-diversity. R platform and GraphPad Prism 7.0 (San Diego, CA) were used for visualizing the results.

Shotgun metagenomic sequencing: The DNA extracted from fecal samples previously used for 16S rRNA sequencing was shotgun metagenome sequenced using an Illumina-based platform for analysis of microbiome functional genes. The functional gene profiling of the shotgun metagenome was performed using HUMAnN2 v0.11.2 pipeline.35 In the preprocessing step, quality filtering of sequencing reads was performed and followed by screening and removal of contaminant host (human) reads. Trimmomatic v0.38 was used for the filtering and trimming of raw sequence data with the default cut-off settings. The reads were searched against a human genome database in paired-end mode using bowtie2 algorithm and were discarded if they were mapped to the database. To obtain the gene family profiles, these quality-controlled metagenome sequences were first searched against a nucleotide database (ChocoPhlAn) using bowtie2 and then against a protein database (UniRef90) using diamond. All the identified gene families were annotated using UniRef90 and pathways using MetaCyc identifiers. α- and β-diversities were generated with the gene family profiles.

The results of the alpha diversity analysis are shown in FIG. 1. In the Figure, the top row of plots represents the subjects receiving vancomycin treatment. The second row of plots represents the subjects receiving 300 mg of ibezapolstat treatment. And the third row of plots represents the subjects receiving 450 mg of ibezapolstat treatment. The fourth row represents the subjects receiving placebo. As can be seen in this Figure, the treatment with ibezapolstat results in less overall change in the alpha diversity of the biome during the course of treatment as compared to vancomycin.

The results of the beta diversity analysis are shown in FIG. 2. In the Figure, the left plot demonstrates the baseline diversity in the subjects prior to treatment. The right plot shows the beta diversity of subjects receiving either vancomycin or ibezapolstat. The subjects receiving ibezapolstat have a beta diversity that stays around the same y-axis, whereas the vancomycin subjects are demonstrating a much different beta diversity. The results of this study demonstrate that the gut diversity is different after administration of ibezapolstat as compared to vancomycin.

Microbiome Analysis

The microbiome of the healthy subjects receiving either ibezapolstat or vancomycin treatment was analyzed using the methods described in Gonzales-Luna (Systems biology evaluation of refractory Clostridioides difficile infection including multiple failures of fecal microbiota transplantation. Anaerobe 2021:102387. DOI: 10.1016/j.anaerobe.2021.102387), and Segata et al. (Metagenomic biomarker discovery and explanation. Genome Biol 2011; 12(6):R60. DOI: 10.1186/gb-2011-12-6-r60).

Using the sequencing described above, we analyzed the bacterial phylum changes over time in the subjects receiving either ibezapolstat or vancomycin. The results of this analysis are shown in FIG. 3. As is evident from the results of this analysis, treatment with vancomycin causes Proteobacteria to "bloom" (shown in dark grey in the plots). Also evident from this analysis, is that treatment with ibezapolstat results in a higher proportion of Actinobacteria.

Figure 4A:
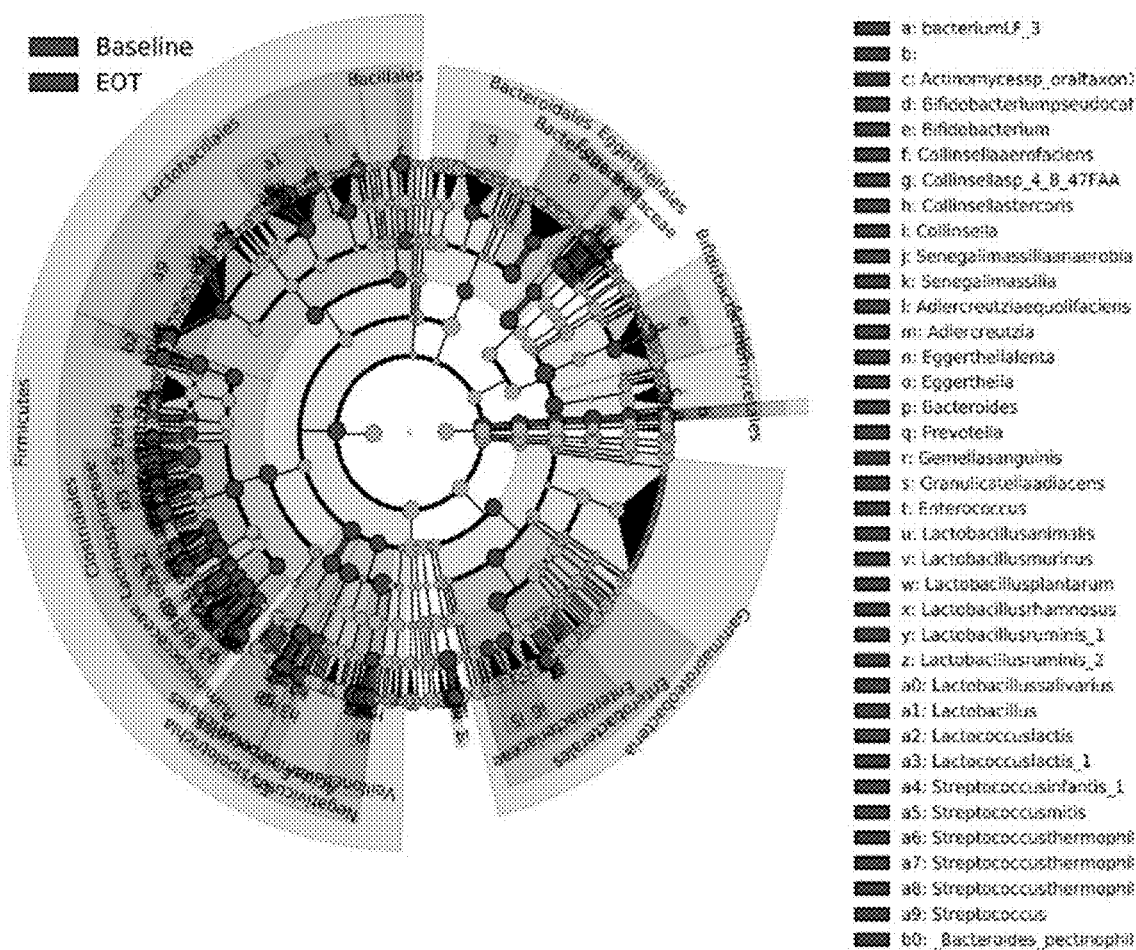
FIGS. 4A and 4B shows a linear effect size algorithm (LEfSe) summary of microbiome changes from day 0 versus day 10 in subjects given ibezapolstat and vancomycin. The shading represents either increased or reduced bacterial abundance on day 10 compared to baseline.
Figure 4B:
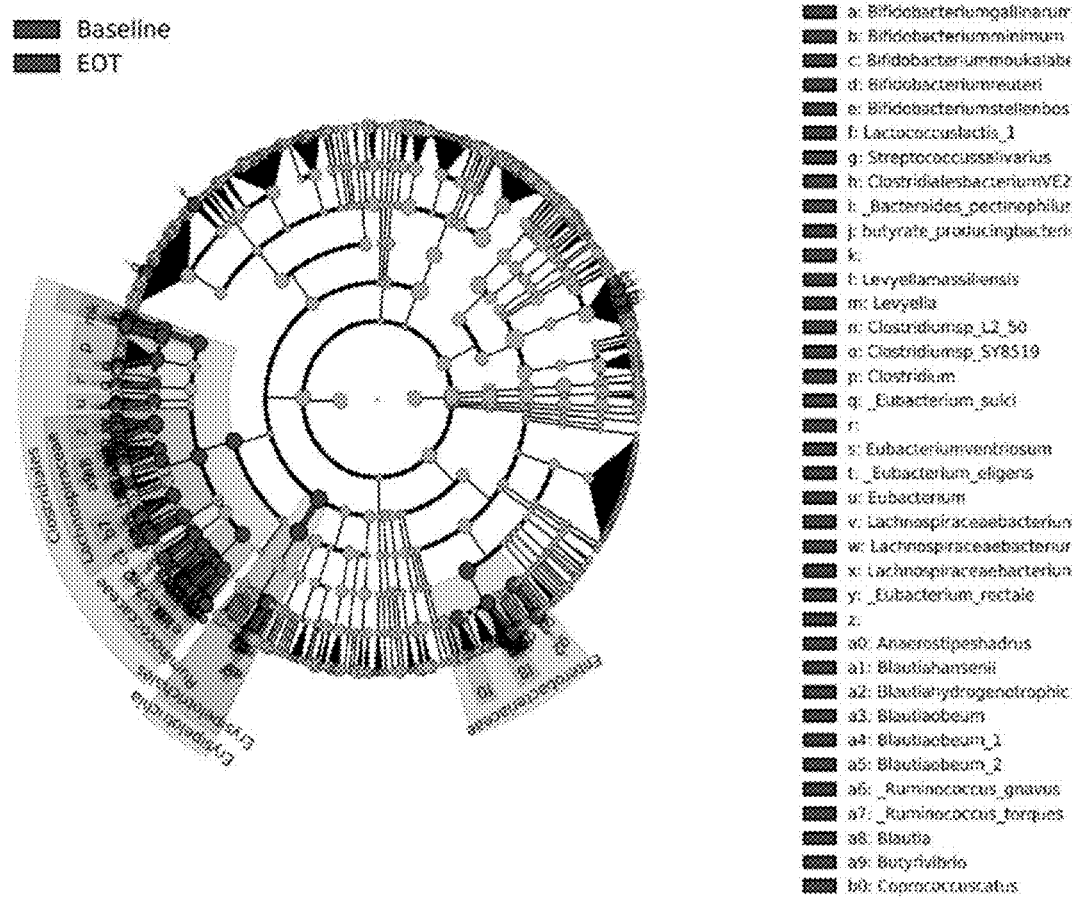

We analyzed the data from the healthy volunteers treated with either ibezapolstat or vancomycin using a linear discriminant analysis effect size (LEfSe) method, which allows for high dimensional class comparisons with a particular focus on metagenomic analyses. This method is described in Segata et al. (Metagenomic biomarker discovery and explanation. Genome Biol 2011; 12(6):R60. DOI: 10.1186/gb-2011-12-6-r60). The results of this analysis are shown in FIG. 4. The Figure depicts the microbiome changes from day 0 versus day 10 in subjects given either ibezapolstat or vancomycin. The shading represents either reduced bacterial abundance on day 10 compared to baseline, or increased abundance. As is evident in the LEfSe plot, ibezapolstat results in much less change to the overall microbiome at day 10 of treatment as compared to the vancomycin at day 10.

Baseline microbiota were not different at baseline (Day 0 samples) for any study group. Individual phylum and Shannon's index alpha diversity daily changes over time for subjects given ibezapolstat, vancomycin, or placebo is shown in FIGS. 1 and 3. Inter-individual phylum differences were evident. However, in general the proportion of Proteobacteria or Fusobacteria increased in subjects given vancomycin while proportion of Actinobacteria increased consistently in subjects given ibezapolstat. In general, alpha diversity decreased on therapy for individual subjects receiving either ibezapolstat or vancomycin compared to placebo. Statistical analysis of alpha diversity changes over time is shown in Table 1 below. Using three separate alpha diversity indices (Shannon, Simpson, and Pielous), ibezapolstat 450 mg and vancomycin showed statistically significant changes in alpha diversity over time compared to placebo. Ibezapolstat 300 mg did not demonstrate statistically significant changes compared to placebo. Summary measures for alpha diversity changes (Shannon's) over time by treatment group is shown in FIG. 6. Beta diversity changes confirmed that microbiota was significantly different between study groups (FIG. 6). Using principle co-ordinate analysis, baseline samples were similar in all study groups while distinct ellipses representing 95% confidence of each cluster were significantly different for vancomycin treated subjects compared to either dose of ibezapolstat or placebo samples. Cladograms at baseline compared to end of therapy generated by the LEfSe algorithm is shown in FIG. 4. Vancomycin had a more wide-ranging effect on the microbiome including significantly lower proportion of most taxa except for an increased proportion of Gammaproteobacteria. Ibezapolstat demonstrated a decreased proportion of Clostridialis and an increased proportion of Enterobacteriaceae and certain species of Bifidobacteriaceae. Bacterial taxa changes at the Phylum, Class, Order, and Family level is shown in Table 2 below.

TABLE 1

Comparison of (A) daily alpha diversity and (B) bile acid changes during therapy for ibezapolstat vs. oral vancomycin

|  | Ibezapolstat 300 mg (*) | Ibezapolstat 450 mg (*) | Vancomycin 125 mg (*) |
|---|---|---|---|
| A. Alpha Diversity Analysis | | | |
| Shannon | −0.12 ± 0.12 (0.31) | −0.45 ± 0.12 (0.0001) | −0.36 ± 0.11 (0.0014) |
| Simpson's | −0.013 ± 0.023 (0.59) | −0.072 ± 0.022 (0.0019) | −0.070 ± 0.023 (0.0020) |
| Pielous | −0.0040 ± 0.024 (0.87) | −0.051 ± 0.024 (0.031) | −0.073 ± 0.024 (0.0016) |
| B. Bile Acid Analysis | | | |
| 1° bile acids, ug/L | −3.7 ± 172 (0.98) | 307 ± 161 (0.061) | 963 ± 146 (<0.001) |
| 2° bile acids, ug/L | −913 ± 675 (0.18) | −971 ± 629 (0.13) | −1,266 ± 570 (0.030) |
| 1°:2° bile acid ratio | −1.3 ± 4.1 (0.75) | 6.2 ± 3.8 (0.11) | 19 ± 3.5 (<0.0001) |

Numbers represent average change ± standard deviation over the study time period.
A negative (−) number represents decreased (A) diversity or (B) bile acid concentrations.
1°: Primary; 2°: secondary; *p value vs placebo controlling for patient age, weight, and sex

TABLE 2

Proportional changes in taxa in healthy subjects given vancomycin or one of two doses of ibezapolstat. Italics indicates at least a 10 percent increase in relative proportion compared to baseline/bold italics represents a 10% decrease in relative proportion (only variables with a p < 0.005 significance colored).

|  | Vancomycin 125 mg | | Ibezapolstat 300 mg | | Ibezapolstat 450 mg | |
|---|---|---|---|---|---|---|
| Taxa (Bold indicates Phylum) | Proportional change (mean ± SE) | P | Proportional change (mean ± SE) | P | Proportional change (mean ± SE) | P |
| Actinobacteria | −0.11 ± 0.05 | 0.032 | *0.31 ± 0.053* | *<0.0001* | *0.31 ± 0.054* | *<0.0001* |
| c_Actinobacteria | −0.074 ± 0.051 | 0.14 | *0.27 ± 0.052* | *<0.0001* | *0.29 ± 0.053* | *<0.0001* |
| c_Actinobacteria o_Bifidobacteriales f_Bifidobacteriaceae | −0.078 ± 0.051 | 0.1293 | *0.27 ± 0.053* | *<0.0001* | *0.29 ± 0.053* | *<.0001* |
| c_Actinobacteria o_Bifidobacteriales | −0.080 ± 0.051 | 0.1201 | *0.27 ± 0.053* | *<.0001* | *0.29 ± 0.053* | *<.0001* |
| c_Coriobacteriia | −0.038 ± 0.015 | 0.0145 | 0.036 ± 0.016 | 0.0221 | 0.024 ± 0.016 | 0.1431 |
| c_Coriobacteriia o_Coriobacteriales | −0.031 ± 0.015 | 0.0375 | 0.035 ± 0.016 | 0.0264 | 0.026 ± 0.016 | 0.1013 |
| c_Coriobacteriia o_Coriobacteriales f_Coriobacteriaceae | −0.032 ± 0.015 | 0.0338 | 0.034 ± 0.016 | 0.0298 | 0.025 ± 0.016 | 0.1122 |
| Bacteroidetes | −0.034 ± 0.024 | 0.16 | −0.0055 ± 0.025 | 0.83 | 0.013 ± 0.025 | 0.61 |
| Firmicutes | −0.14 ± 0.058 | 0.014 | *−0.47±0.060* | *<0.0001* | *.0.30±0.06* | *<0.0001* |
| c_Clostridia | *−0.50±0.052* | *<0.0001* | *−0.49±0.054* | *<0.0001* | *~0.52±0.054* | *<0.0001* |
| c_Clostridia o_Clostridiales | *−0.50±0.052* | *<.0001* | *−0.49±0.054* | *<.0001* | *~0.52±0.054* | *<.0001* |
| c_Clostridia o_Clostridiales f_Lachnospiraceae | *.0.24±0.024* | *<.0001* | *−0.22±0.025* | *<.0001* | *−0.26±0.023* | *<.0001* |
| c_Clostridia o_Clostridiales f_Ruminococcaceae | *~0.25±0.033* | *<.0001* | *~0.27±0.034* | *<.0001* | *−0.25±0.035* | *<.0001* |
| c_Bacilli | *0.30 ± 0.043* | *<0.0001* | 0.016 ± 0.044 | 0.72 | 0.017 ± 0.045 | 0.39 |
| c_Bacilli o_Lactobacillales | *0.30 ± 0.043* | *<.0001* | 0.016 ± 0.044 | 0.7117 | 0.017 ± 0.045 | 0.6972 |
| c_Bacilli o_Lactobacillales f_Lactobacillaceae | *0.28 ± 0.041* | *<.0001* | 0.024 ± 0.042 | 0.5755 | 0.015 ± 0.043 | 0.7307 |
| Fusobacteria | 0.036 ± 0.015 | 0.0165 | 0.0011 ± 0.015 | 0.9414 | 0.00046 ± 0.015 | 0.9762 |
| Proteobacteria | *0.23 ± 0.045* | *<0.0001* | 0.12 ± 0.05 | 0.0094 | 0.09 ± 0.05 | 0.053 |
| c_Gammaproteobacteria | *0.21 ± 0.045* | *<0.0001* | 0.12 ± 0.046 | 0.0094 | 0.092 ± 0.046 | 0.0478 |
| c_Gammaproteobacteria o_Enterobacterales | *0.17 ± 0.042* | *<0.0001* | 0.11 ± 0.043 | 0.0099 | 0.094 ± 0.044 | 0.0336 |
| c_Gammaproteobacteria o_Enterobacterales f_Enterobacteriaceae | *0.17 ± 0.041* | *<0.0001* | 0.11 ± 0.042 | 0.0082 | 0.087 ± 0.043 | 0.043 | c: Class; o: Order; f: Family

Bile Acid Analysis

To further analyze bile acid changes associated with ibezapolstat use, a LC-MS-MS method was developed for this study based on published data in both Scherer M, et al. (Rapid quantification of bile acids and their conjugates in serum by liquid chromatography-tandem mass spectrometry. J Chromatogr B Analyt Technol Biomed Life Sci 2009; 877(30):3920-5. DOI: 10.1016/j.jchromb.2009.09.038), and Qian X et al. (Ridinilazole, a narrow spectrum antibiotic for treatment of *Clostridioides difficile* infection, enhances preservation of microbiota-dependent bile acids. Am J Physiol Gastrointest Liver Physiol 2020; 319(2):G227-G237. DOI: 10.1152/ajpgi.00046.2020).

Figure 8:
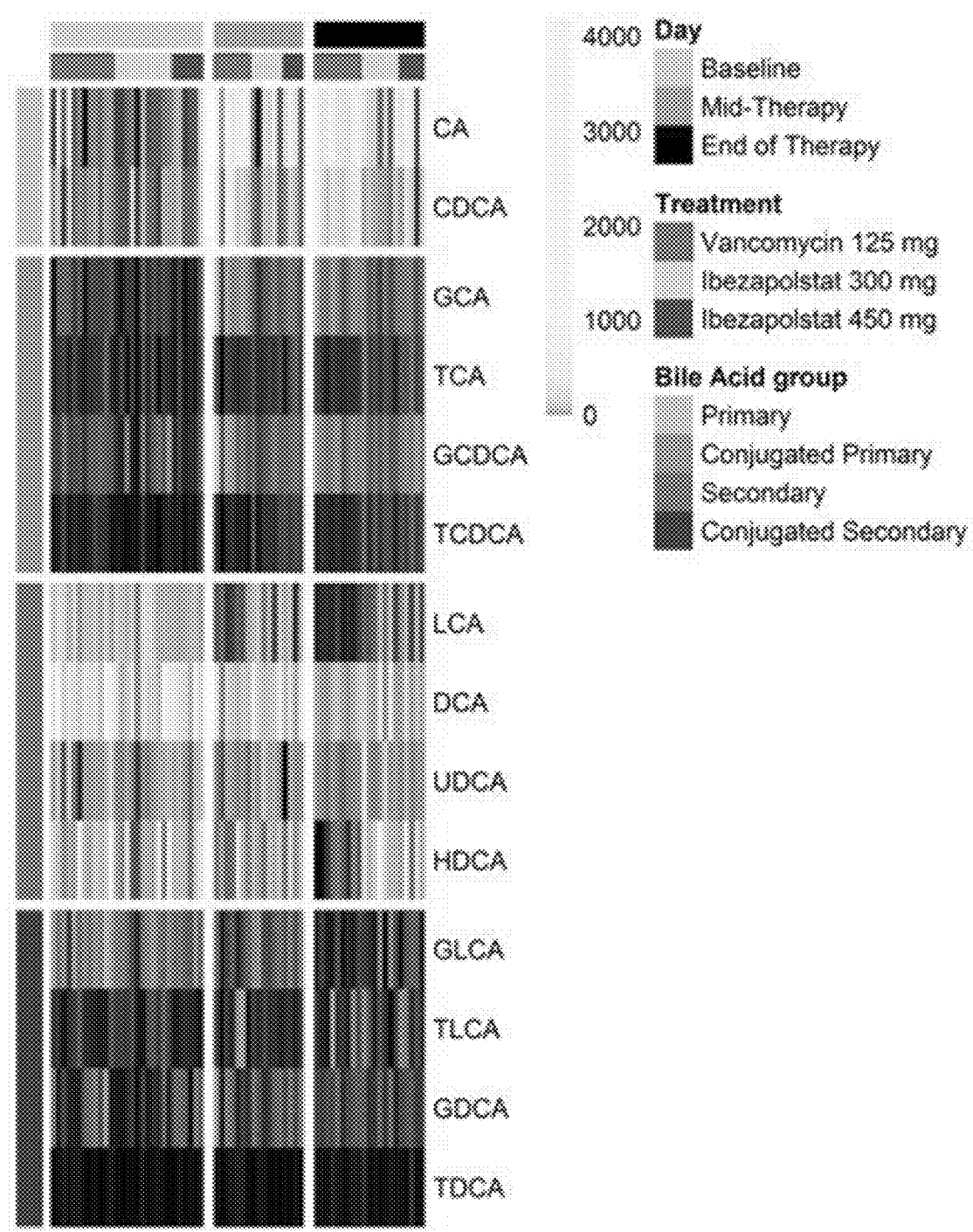
FIG. 8 shows bile acid concentrations from IBZ- and VAN-treated subjects at baseline, mid-point of therapy, and end-of-therapy.
Figure 9:
FIG. 9 shows ibezapolstat trial results showing clinical cure and sustained clinical cure following administration of ibezapolstat.

Seventeen baseline samples were available for bile acid analysis, 17 day five samples, and 14 day 10 samples. Concentrations of bile acids for each drug and time period is shown in FIG. 8. Baseline samples were similar for all study groups and comprised primarily (>95%) of secondary bile acids. Primary bile acids increased and secondary bile acids decreased with exposure to all study drugs (FIG. 7). Using linear regression analysis controlling for subject demographics, vancomycin was associated with significant increases in primary bile acids as well as primary:secondary bile acid ratios. Although, similar effects were noted with ibezapolstat 450 mg, these results were not statistically significant (Table 1 above).

Figure 5A:
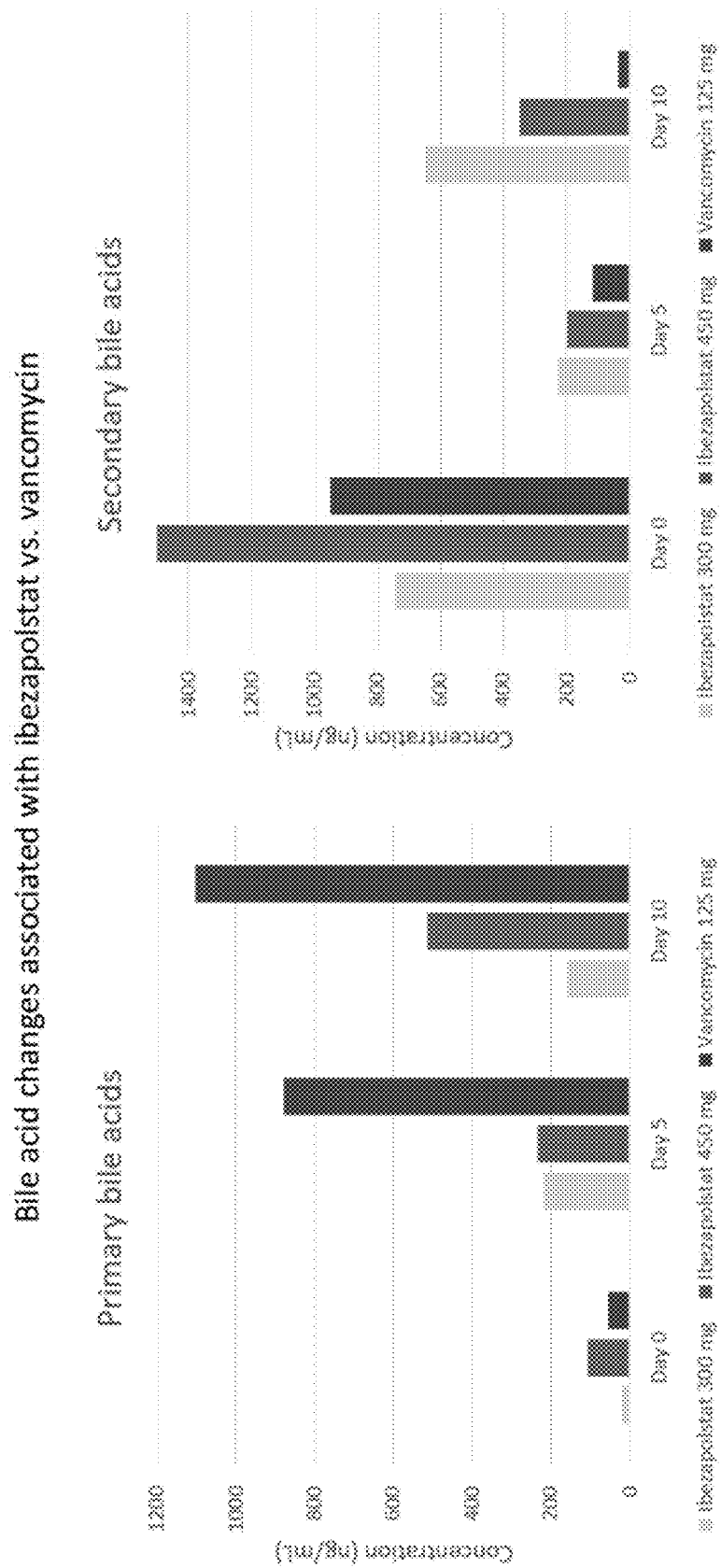
FIGS. 5A and 5B show changes in primary and secondary bile acids associated with administration of ibezapolstat and vancomycin, with FIG. 5B showing the data in the form of a ratio of primary to secondary bile acids.
Figure 5B:
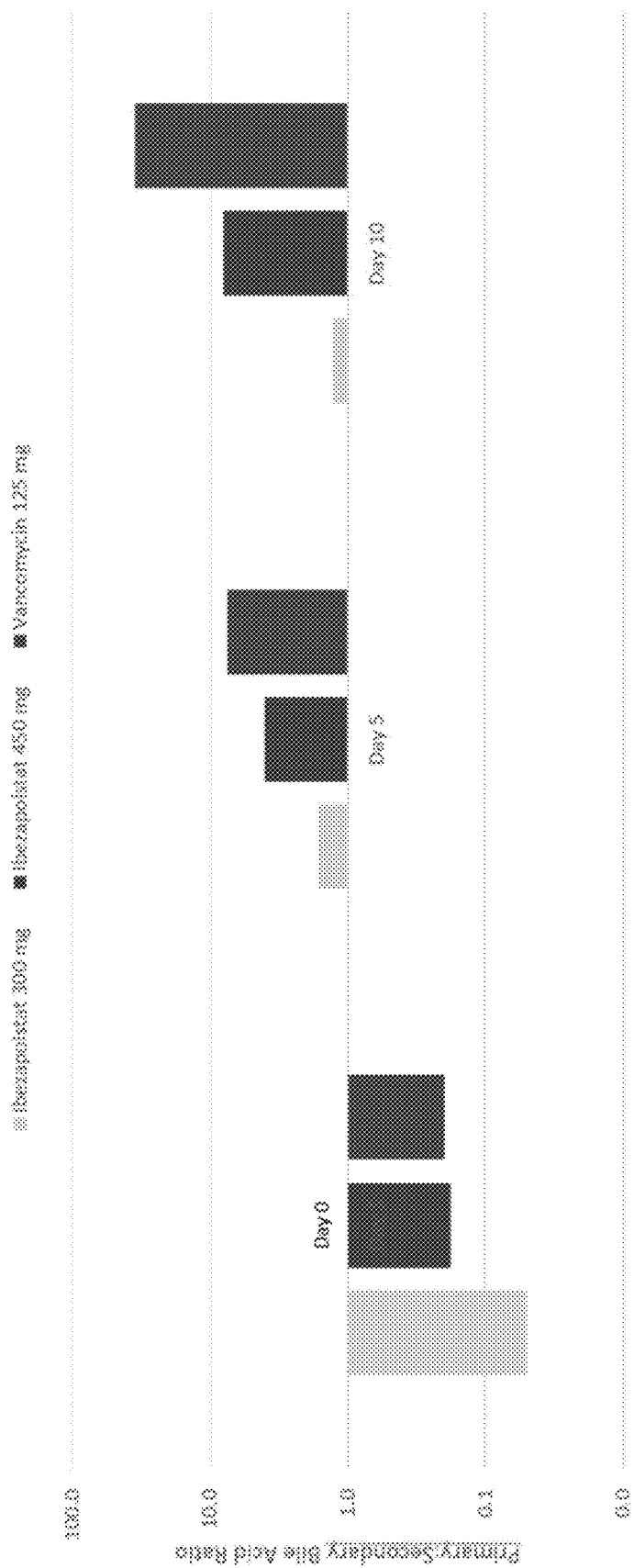
Figure 6A:
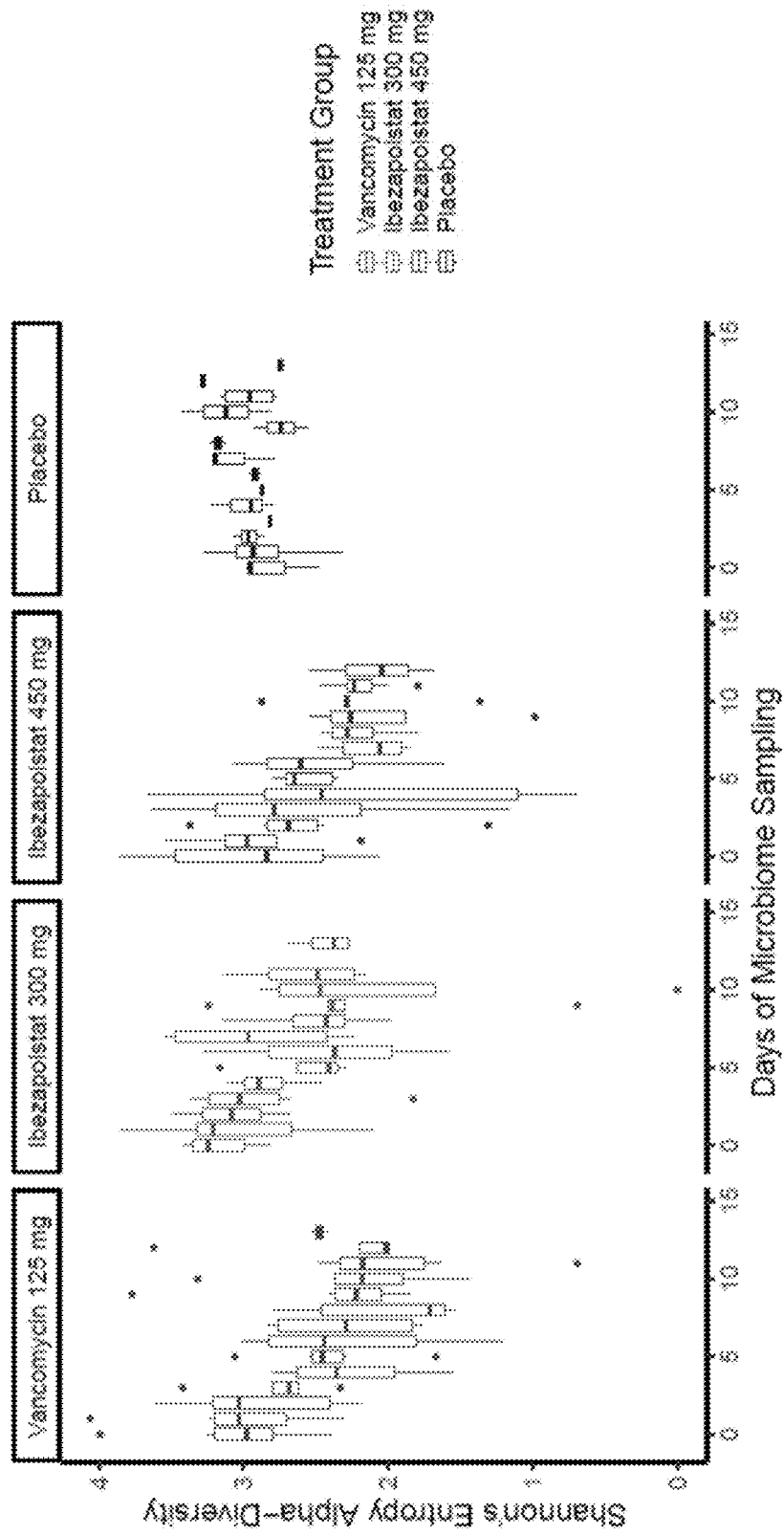
FIG. 6 shows summary estimates of alpha diversity over time by treatment group measured by Shannon's Entropy (6A) or Simpson's Index (6B) and beta diversity measured at baseline (6C) or after at least 5-days of therapy (6D).
Figure 6B:
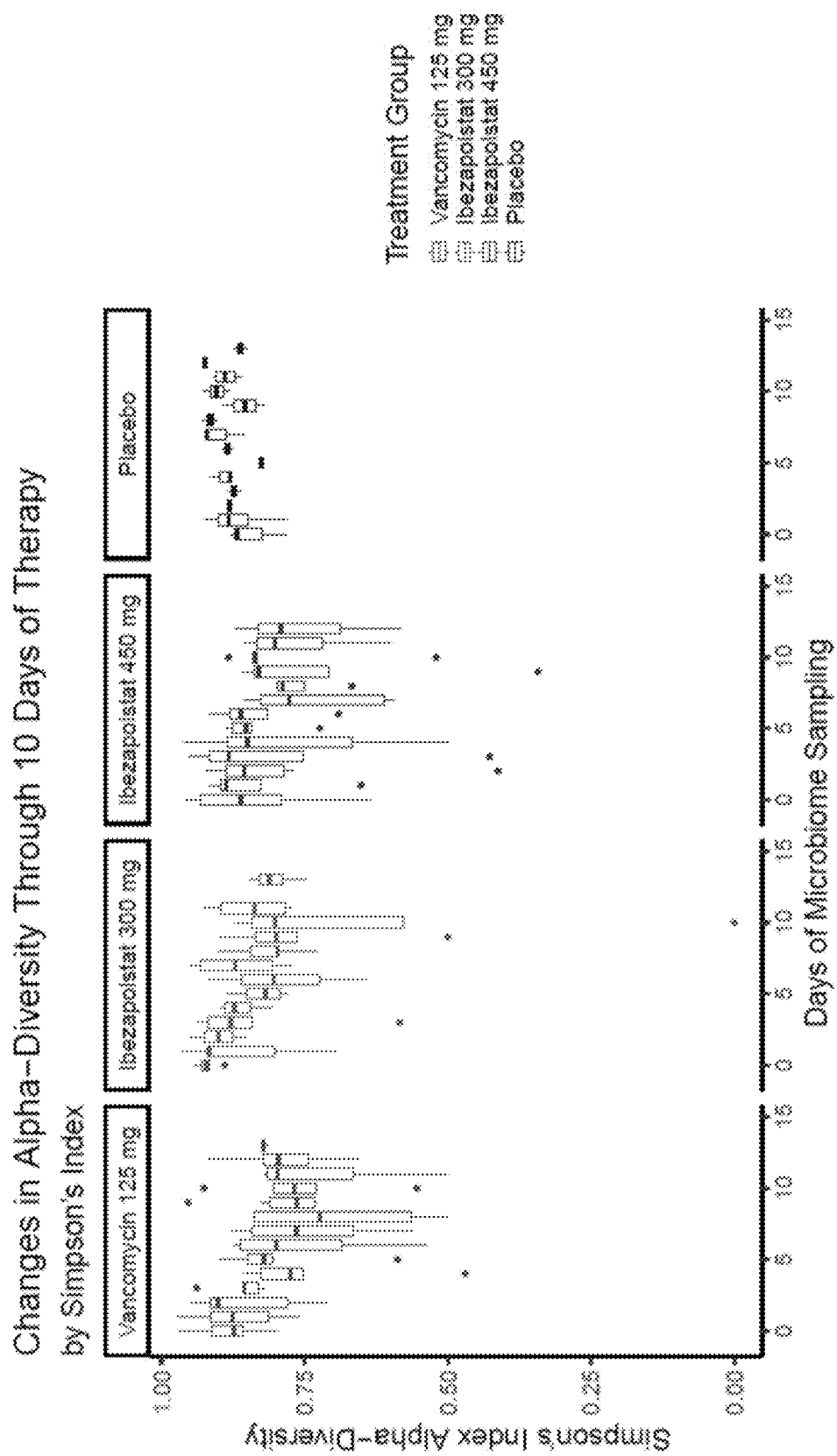
Figure 6C:
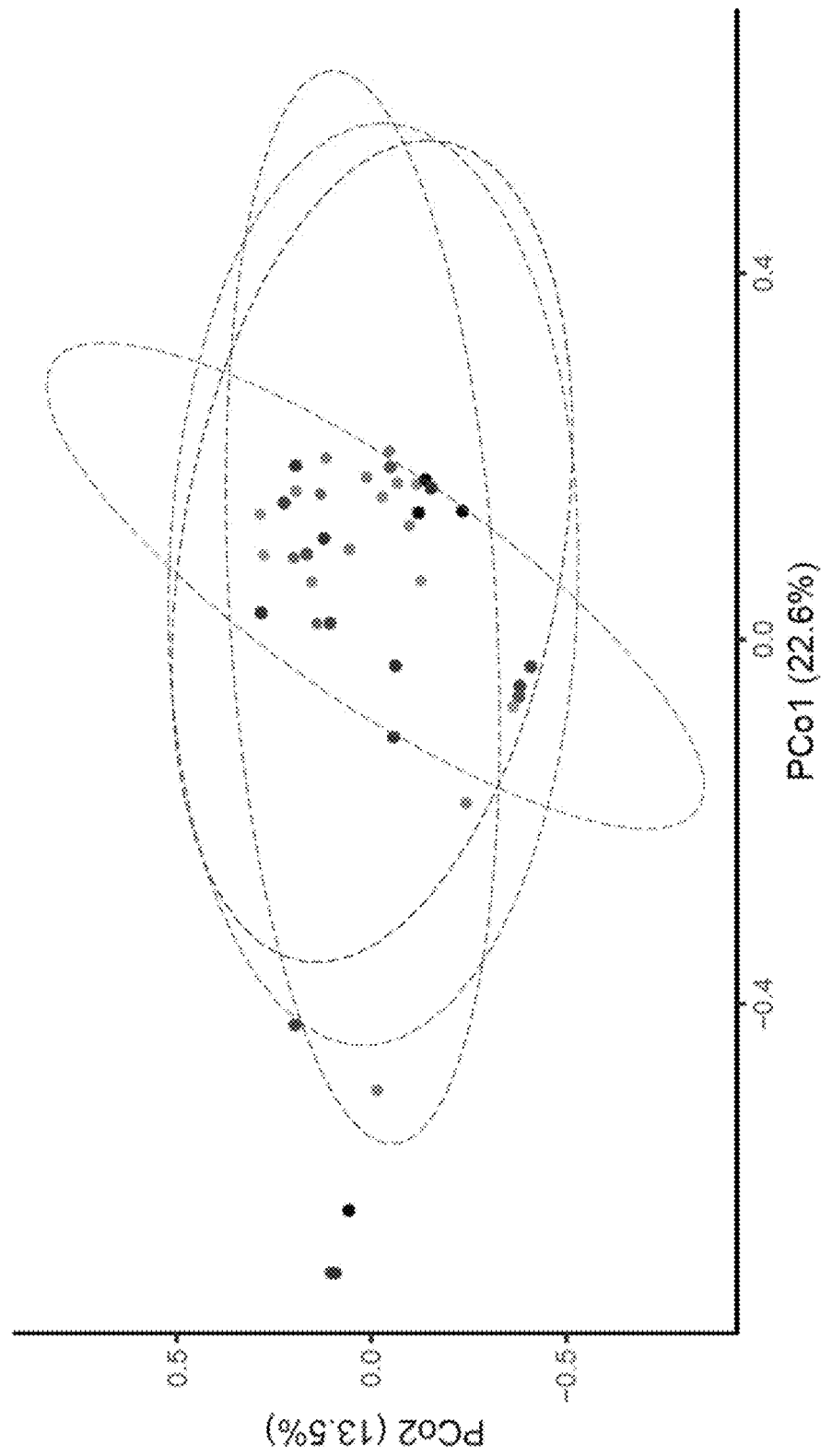
Figure 6D:
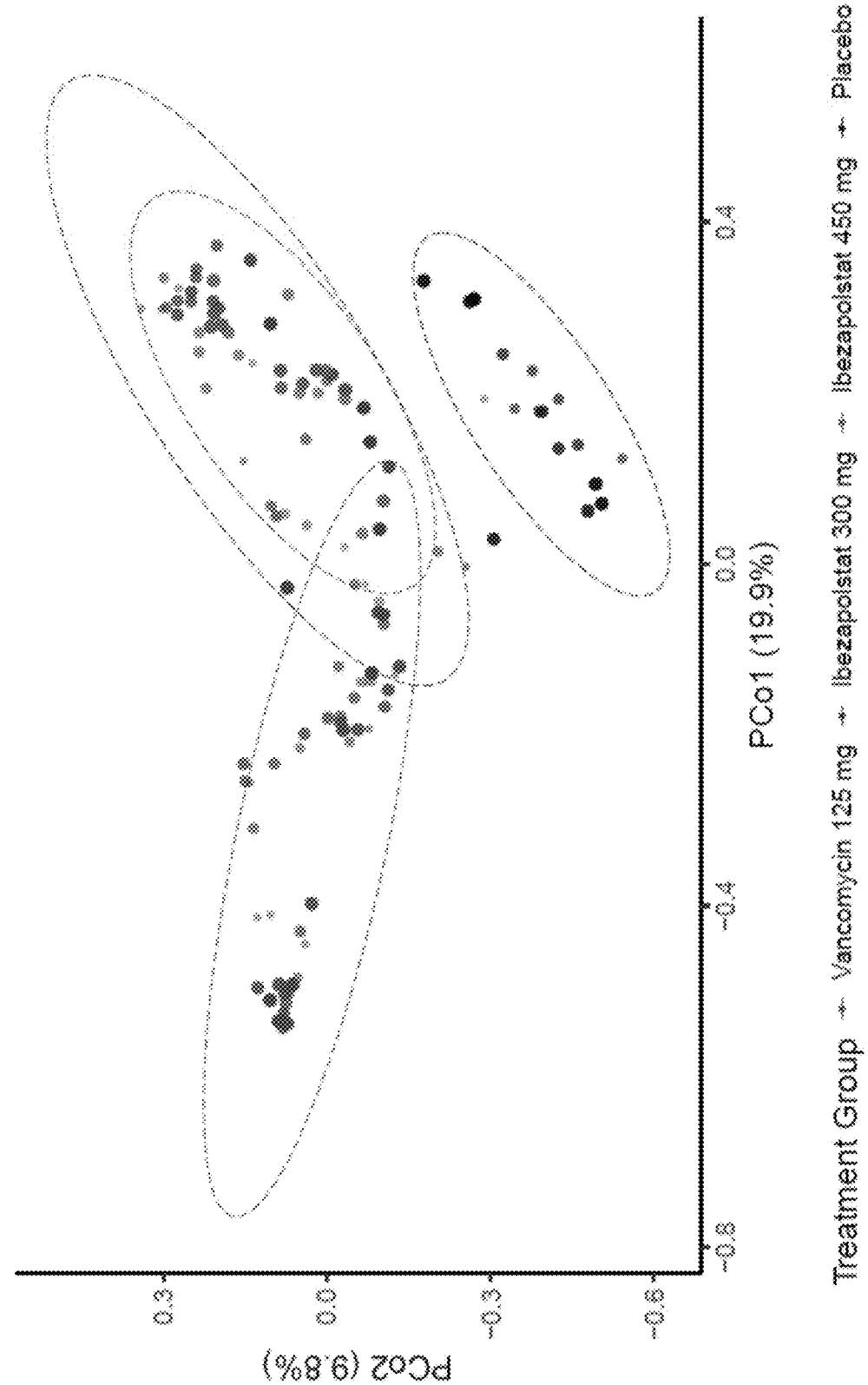

The results of this analysis are shown in FIGS. 5A and 5B. The left plot shows the change in primary bile acids during the course of treatment with either ibezapolstat or vancomycin. The right plot shows the change in secondary bile acids during the course of treatment with either ibezapolstat or vancomycin. As is evident from these results, treatment with vancomycin causes a large increase in primary bile acids, while also causing a large decrease in secondary bile acids. In contrast, ibezapolstat does not cause a significant change to the amount of primary bile acids, and does not cause the same large decrease in secondary bile acids.

Correlation Between Microbiota and Bile Acid Changes

Correlation between Family taxa and primary and secondary bile acid concentrations is shown in Table 3. Enterobacteriaceae were most highly correlated with primary bile acid concentrations (r:0.63; p<0.0001) while Ruminococcaceae were negatively correlated with primary bile acid concentrations (r:−0.37;p=0.0025). Ruminococcaceae were also positively correlated with secondary bile acid concentrations (r:0.44; p=0.0002). Pseudomonadaceae were also positively correlated with secondary bile acid concentrations (r:0.38; p=0.0017).

TABLE 3

Correlation of microbiota with bile acids.

| Family | Primary Bile Acids | P | Secondary Bile Acids | P |
|---|---|---|---|---|
| Bacteroidaceae | −0.20096 | 0.103 | −0.10486 | 0.3984 |
| Bifidobacteriaceae | −0.07082 | 0.569 | −0.03019 | 0.8084 |
| Coriobacteriaceae | −0.23574 | 0.0548 | −0.02838 | 0.8197 |
| Enterobacteriaceae | 0.62888 | <.0001 | −0.16676 | 0.1774 |
| Erysipelotrichaceae | −0.12744 | 0.3041 | −0.03216 | 0.7962 |
| Fusobacteriaceae | −0.0662 | 0.5946 | −0.04921 | 0.6925 |
| Lachnospiraceae | −0.33184 | 0.0061 | 0.01017 | 0.9349 |
| Lactobacillaceae | 0.26868 | 0.0279 | −0.09527 | 0.4432 |
| Methanobacteriaceae | 0.00194 | 0.9876 | −0.01041 | 0.9333 |
| Pseudomonadaceae | 0.27146 | 0.0263 | 0.37721 | 0.006 |
| Ruminococcaceae | −0.36391 | 0.0025 | 0.44424 | 0.0002 |

Important metagenomic findings in this study were a consistent decrease in Clostridia class with both antibiotics but then an expansion of Actinobacteria class in ibezapolstat treated subjects and an expansion of Gammaproteobacteria class, Enterobacterales order, and Enterobacteriaceae family in vancomycin treated subjects. Within the Firmicute phylum, vancomycin was also associated with an increased proportion of Bacilli class taxa.

Example 2

Microbiome Data from Phase 2a Clinical Trial of Ibezapolstat for CDI

Phase 2 Clinical Trials:

The Phase 2 clinical trial is designed to evaluate ibezapolstat in the treatment of CDI.

Phase 2a of this trial was an open-label cohort of 10 subjects from study centers in the United States. In this cohort, 10 patients with diarrhea caused by mild/moderate *C. difficile* diagnosed via toxin EIA+ were treated with ibezapolstat 450 mg orally, twice daily for 10 days. All patients were followed for recurrence for 28±2 days. Stool was collected during course of therapy and at follow up. Patient fecal samples were evaluated for *C. difficile* culture and microbiome changes. The study demonstrated 100% clinical cure at day 12 and 100% sustained clinical cure at day 38. Favorable microbiome changes included overgrowth of Actinobacteria and Firmicutes phylum species while on therapy. These findings demonstrate beneficial effects on bile acid metabolism, and further support that microbiome effects may be predictive of beneficial patient outcomes including low rates of recurrence.

The infection was eliminated 100% with no recurrences of infection (100%), and with an acceptable adverse event profile.

Methods:

Safety Assessments

Safety evaluations included AE assessment, physical examination, vital signs, clinical laboratory tests (chemistry, hematology, and urinalysis), and electrocardiography. Safety endpoints for all subjects were recorded including nature, frequency, and severity of AEs. AEs were assessed at each visit beginning from the time of enrollment and classified according to the Medical Dictionary for Regulatory Activities (MedDRA version 15.0). AE severity (mild, moderate, or severe) and causality (unrelated, possibly related, or probably related to the study medication) were assessed by the investigator at each site.

PK Evaluations

Plasma levels were drawn at 2 and 4 hours after the first daily ibezapolstat administration on days 1, 5, and 10. Fecal samples were collected at baseline and daily during days 1-10 of ibezapolstat receipt. Plasma and fecal concentrations were assayed by AltaSciences (Laval, Quebec, Canada) and PK analyses were performed by Learn and Confirm Inc. (Montreal, Quebec, Canada).

Microbiology

Stool samples were cultured for *C. difficile* growth on a selective cycloserine-cefoxitin fructose agar (CCFA) at 37° C. under anaerobic conditions for 48 hours. (Gonzales-Luna). Isolates were determined to be *C. difficile* based on growth and morphology and confirmed by PCR for *C. difficile* toxin and tpi genes. *C. difficile* was strain typed using a PCR-based ribotyping method as previously described. (Gonzales-Luna A J, Carlson T J, Dotson K M, et al. PCR ribotypes of *Clostridioides difficile* across Texas from 2011 to 2018 including emergence of ribotype 255. Emerg Microbes Infect 2020; 9(1): 341-7.) Minimum inhibitory concentrations (MICs) were determined for ibezapolstat by broth microdilution in 0.1% sodium taurocholate Brain Heart Infusion (BHI) media. (Begum K, Basseres E, Miranda J, et al. In Vitro Activity of Omadacycline, a New Tetracycline Analog, and Comparators against *Clostridioides difficile*. Antimicrob Agents Chemother 2020; 64(8).)

Microbiome and Bile Acid Evaluations

Fecal samples for microbiome analysis were collected daily during ibezapolstat dosing and on days 2, 10, 20, and 28 after EOT. Stool DNA extraction was performed via Qiagen DNeasy PowerSoil Pro Kit (Qiagen, cat #12888-100) in a QIAcube automated DNA extraction system (Qiagen) according to instructions. Microbiome characterization was performed by sequencing the V1-V3 region of the 16S rRNA gene using the MiSeq system (Illumina, San Diego, CA, USA). (Fadrosh D W, Ma B, Gajer P, et al. An improved dual-indexing approach for multiplexed 16S rRNA gene sequencing on the Illumina MiSeq platform. Microbiome 2014; 2(1): 6; Walker J N, Hanson B M, Pinkner C L, et al. Insights into the Microbiome of Breast Implants and Periprosthetic Tissue in Breast Implant-Associated Anaplastic Large Cell Lymphoma. Sci Rep 2019; 9(1): 10393.) Each sample was amplified using a barcoded primer, which yielded a unique sequence identifier tagged onto each individual sample library. Genomic DNA (gDNA) was normalized prior to PCR and PCR products were normalized prior to pooling. Illumina-based sequencing yielded >15,000 reads per sample. Bile acids were quantified using targeted liquid chromatography mass spectrometry (LC-MS) analysis performed on a QTRAP 5500 mass spectrometer (Sciex, Framingham, MA, USA) adapted from a previously described method. (Scherer M, Gnewuch C, Schmitz G, Liebisch G. Rapid quantification of bile acids and their conjugates in serum by liquid chromatography-tandem mass spectrometry. J Chromatogr B Analyt Technol Biomed Life Sci 2009; 877(30): 3920-5.) Bile acid levels were normalized by the corresponding stool sample weight.

Efficacy Assessments

The primary efficacy outcome measure was clinical cure at EOT defined as resolution of diarrhea in the 24-hour period preceding EOT and maintained for at least 48 hours post EOT. SCC was defined as clinical cure with no recurrence of CDI within 28 (±2) days after EOT.

Statistical Analysis

An intent-to-treat analysis of patients receiving at least one dose of ibezapolstat was conducted. Descriptive statistics were calculated for efficacy, safety/tolerability, and PK data generated using SAS version 9.4 software (SAS Institute, Inc Cary, NC, USA). Microbiome summary plots and data visualization was prepared using R software version 4.1.1 (R Core Team 2021, Vienna, Austria). (R Core Team (2013). R: A language and environment for statistical computing. R Foundation for Statistical Computing, Vienna, Austria.) Alpha diversity for each sample was assessed with the VeganR package version 2.4-2 using the Shannon Diversity Index and Inverse Simpson Index. Differences in alpha diversity (Shannon Diversity and Inverse Simpson Indexes) and bile acids at baseline compared to during or after therapy were compared using linear regression models. Proportional changes of bacterial taxa over the 10-day dosing interval were calculated using linear regression models for taxa with at least a one percent proportional change during the study time period. A p value <0.05 was considered significant.

Results of Phase 2a Clinical Trial:

The phase 2a data demonstrated complete eradication of colonic *C. difficile* by day three of treatment with ibezapolstat as well as the observed overgrowth of healthy gut microbiota, Actinobacteria and Firmicute phyla species, during and after therapy. Additionally, the data demonstrated an increased proportion of healthy microbiota including *Clostridiales* order taxa, which are known to metabolize primary bile acids to secondary bile acids via the 7α-dehydroxylation pathway. (Ridlon J M, Kang D J, Hylemon P B. Bile salt biotransformations by human intestinal bacteria. J Lipid Res 2006; 47(2): 241-59). These data show an increased concentration of secondary bile acids during and following ibezapolstat therapy which correlates with colonization resistance against *C. difficile*. Additionally, a decrease in primary bile acids and the favorable increase in the ratio of secondary-to-primary bile acids show that ibezapolstat may reduce the likelihood of CDI recurrence when compared to vancomycin.

Patients

Ten patients aged 49 (±15) years (50% female; 100% white race; 80% Hispanic or Latino ethnicity) were enrolled. All ten patients received ibezapolstat and completed the study. Median number of unformed bowel movements in the 24 hours prior to start of therapy was 4 (range: 3-10). Two of 10 patients received <24 hours of antibiotics, either metronidazole or vancomycin, prior to starting ibezapolstat. No patients were hospitalized prior to or following enrollment.

Safety

A summary of the AEs is provided in Table 4. Seven AEs were reported in 4 of the 10 patients, with 4 of those events occurring in a single subject. None of the events were serious AEs. The severity of AEs was mild (n=2), moderate (n=4), and severe (n=1; drug-unrelated migraine headache). The most common AEs were headache (n=2) or nausea (n=2); both episodes of nausea were regarded by the investigator as 'probably related' to the study drug. No treatment was required for these AEs and no AE required a change to the study drug schedule or withdrawal of dosing. All AEs were resolved by the end of the study.

PK Results

Figure 10:
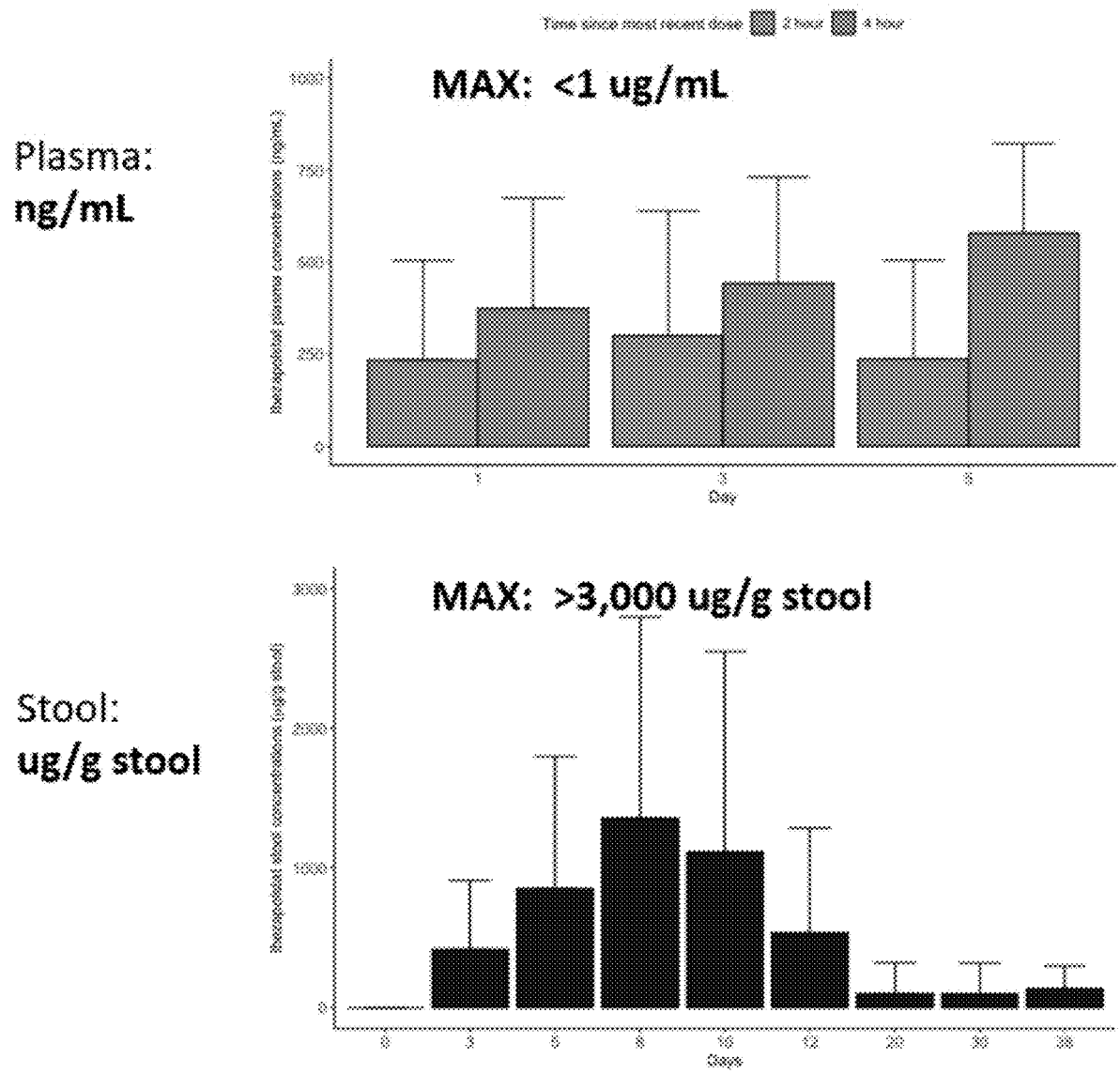
FIG. 10 shows ibezapolstat PK Properties for GI infections. As shown in the figure, ibezapolstat has ideal PK properties for GI infections.
Figure 11:
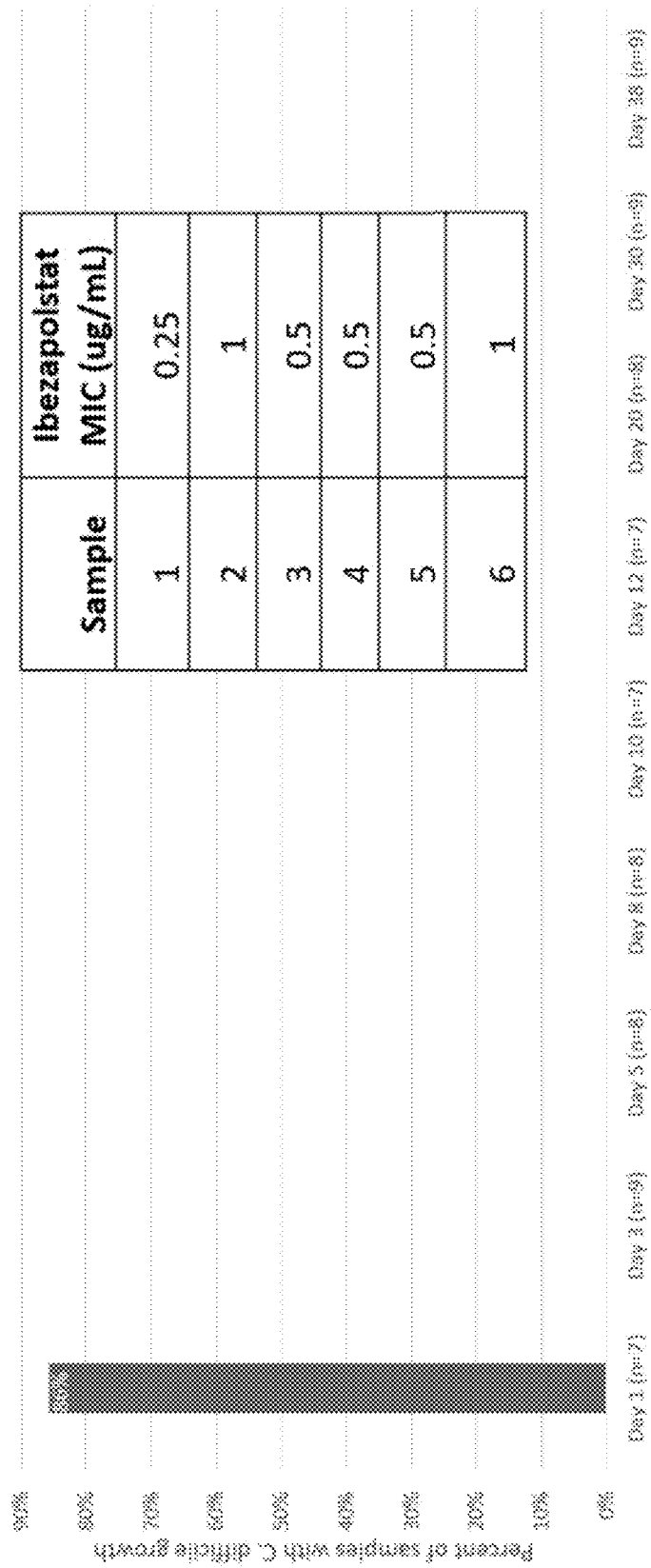
FIG. 11 shows samples treated with ibezapolstat that underwent a 48-hour enrichment step with taurocholate prior to plating on CCFA plates.

Two- to four-hour post-dose ibezapolstat plasma levels ranged from 233 to 578 ng/mL with higher concentrations observed at the 4-hour postdose time period (range: 373-578 ng/mL) compared to the 2-hour post-dose time period (range: 234-299 ng/mL). By day 3 of therapy, ibezapolstat stool concentrations averaged 416±494 μg/g stool and increased to >1,000 μg/g stool by days 8-10 of therapy. Concentrations averaged 535±748 μg/g stool two days after EOT. Three of 4 stool samples collected on day 38 continued to have detectable stool concentrations of ibezapolstat (136±161 μg/g stool). Full stool and plasma PK data are shown in FIG. 10. Ibezapolstat achieved high stool concentrations and plasma concentrations that did not exceed 1 ug/mL.

Microbiology Results

Seven baseline stool samples were available for microbiology studies, of which 6 (86%) grew toxigenic *C. difficile*. Stool samples from all other sampling days (range 7-9 samples/day) did not grow *C. difficile*. Identified ribotypes included F078-126 (n=2), F014-020 (n=2), F106 (n=1), and FP435 (n=1). Ibezapolstat MICS were 0.25 (n=1), 0.5 (n=3), or 1.0 (n=1) ug/mL.

Microbiome and Bile Acid Results

Figure 12A:
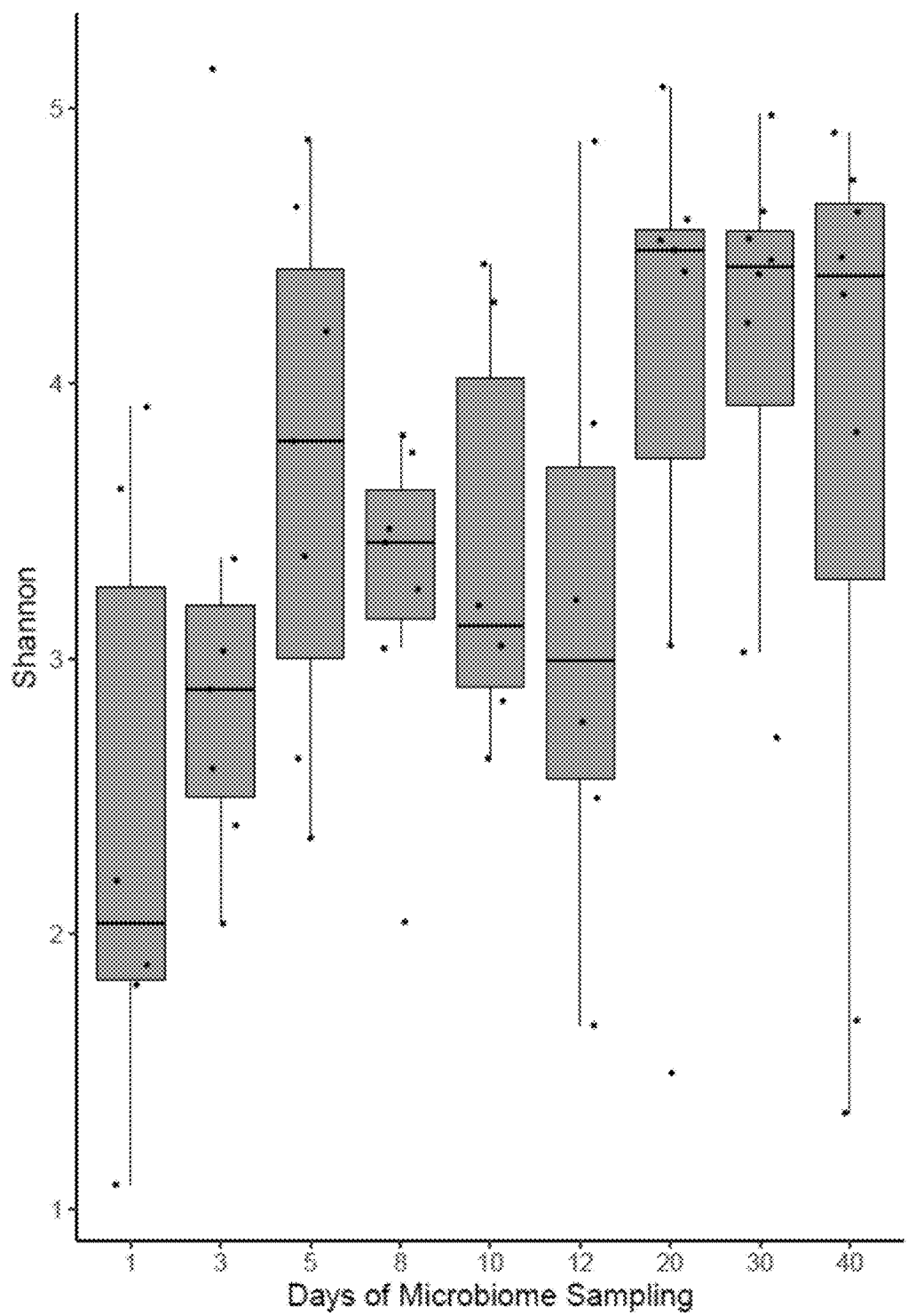
FIGS. 12A and 12B show summary estimates of alpha diversity over time following administration of ibezapolstat measured by Shannon Diversity Index (12A) or measured by Inverse Simpson Index (12B). As shown in the figures, alpha diversity improved while on Ibezapolstat.
Figure 12B:
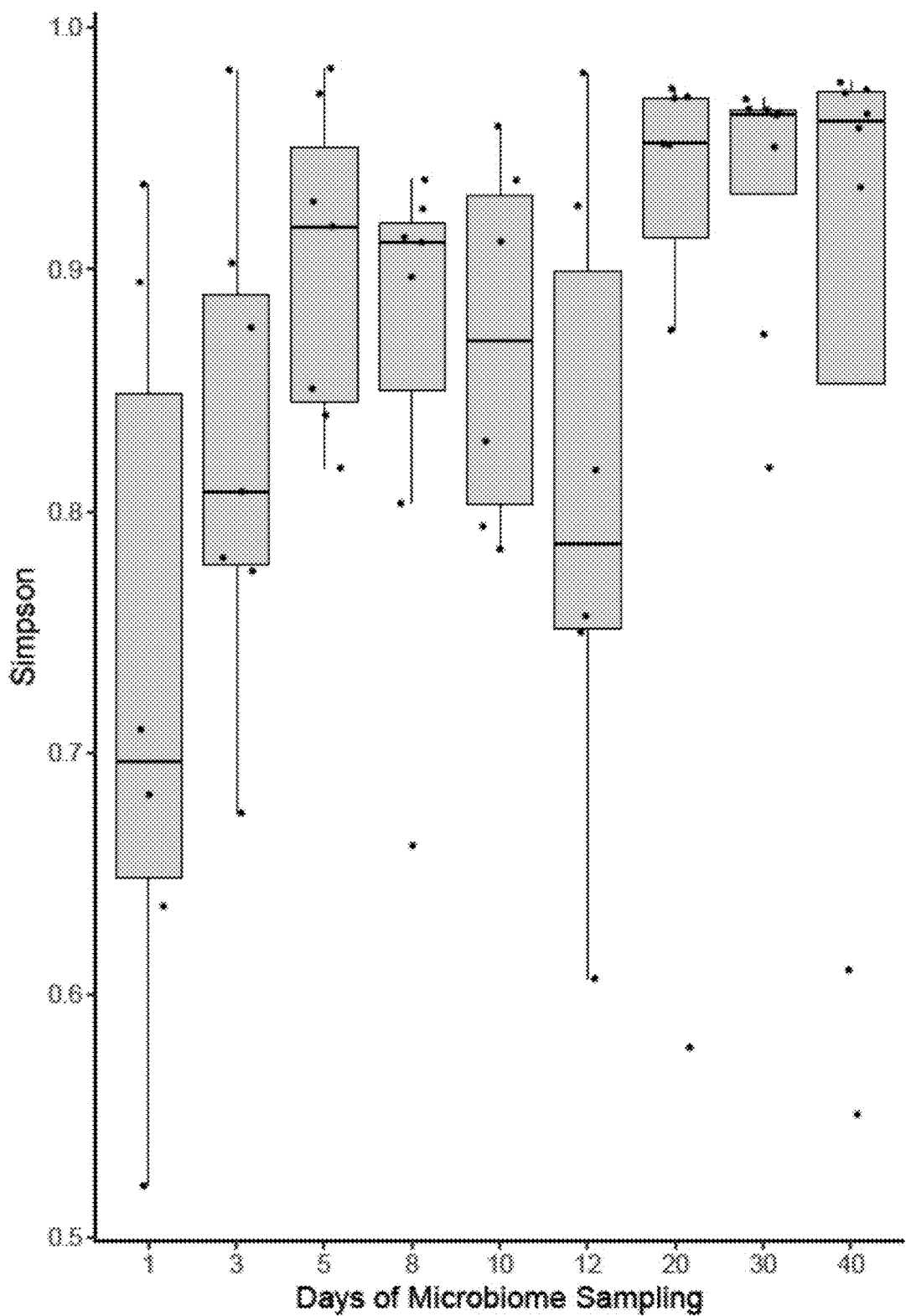
Figure 13A:
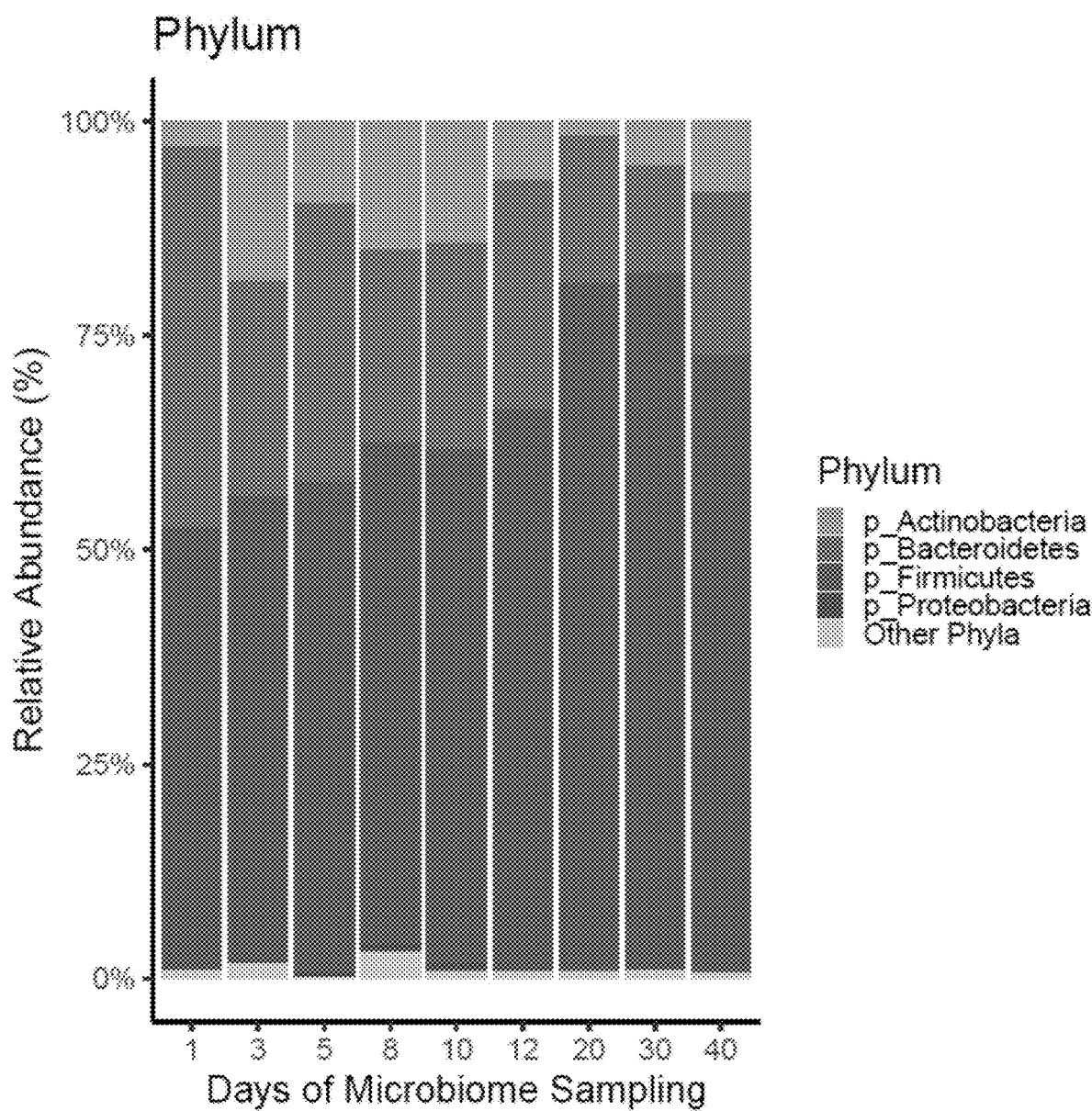
FIGS. 13A-13D show charts comparing mean proportional phylum abundance vs. days of antibiotic therapy (13A); mean proportional class abundance vs. days of antibiotic therapy (13B); mean proportional order abundance vs. days of antibiotic therapy (13C); and mean proportional family abundance vs. days of antibiotic therapy (13D). As shown in the figures, an increased proportion of Firmicutes was observed on ibezapolstat therapy, with the most common increased taxa of firmicutes being Clostridiales.
Figure 13B:
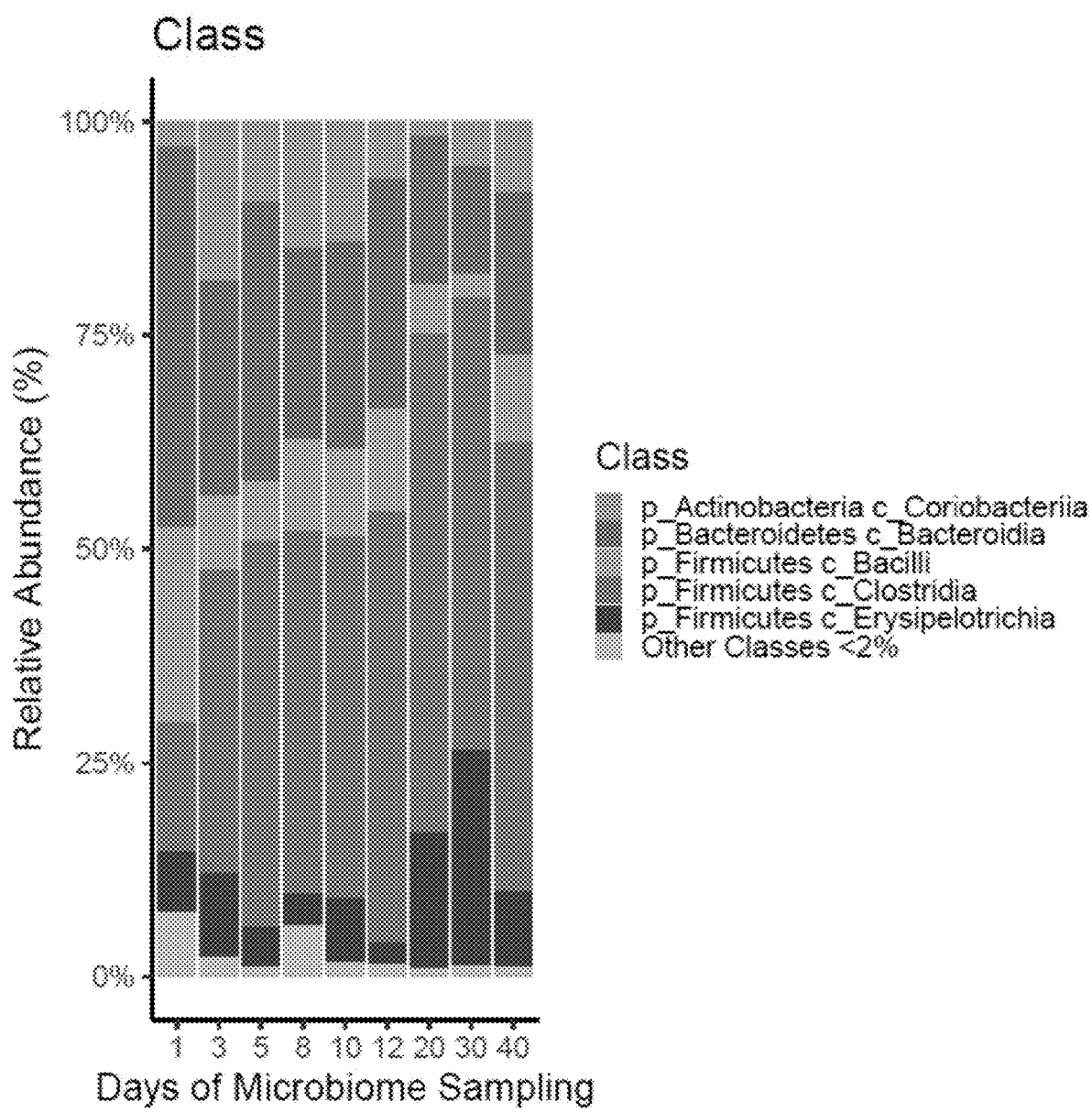
Figure 13C:
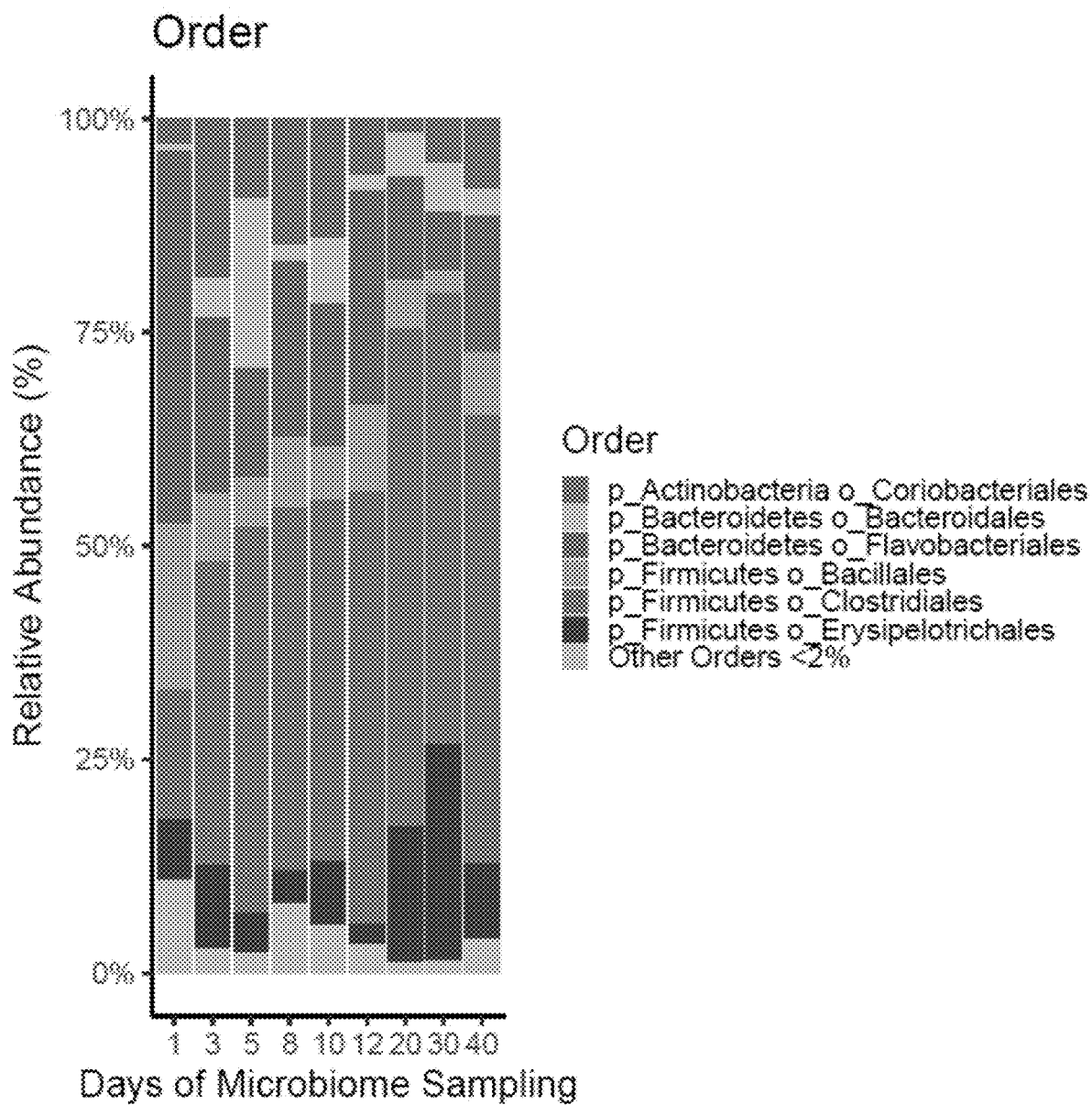
Figure 13D:
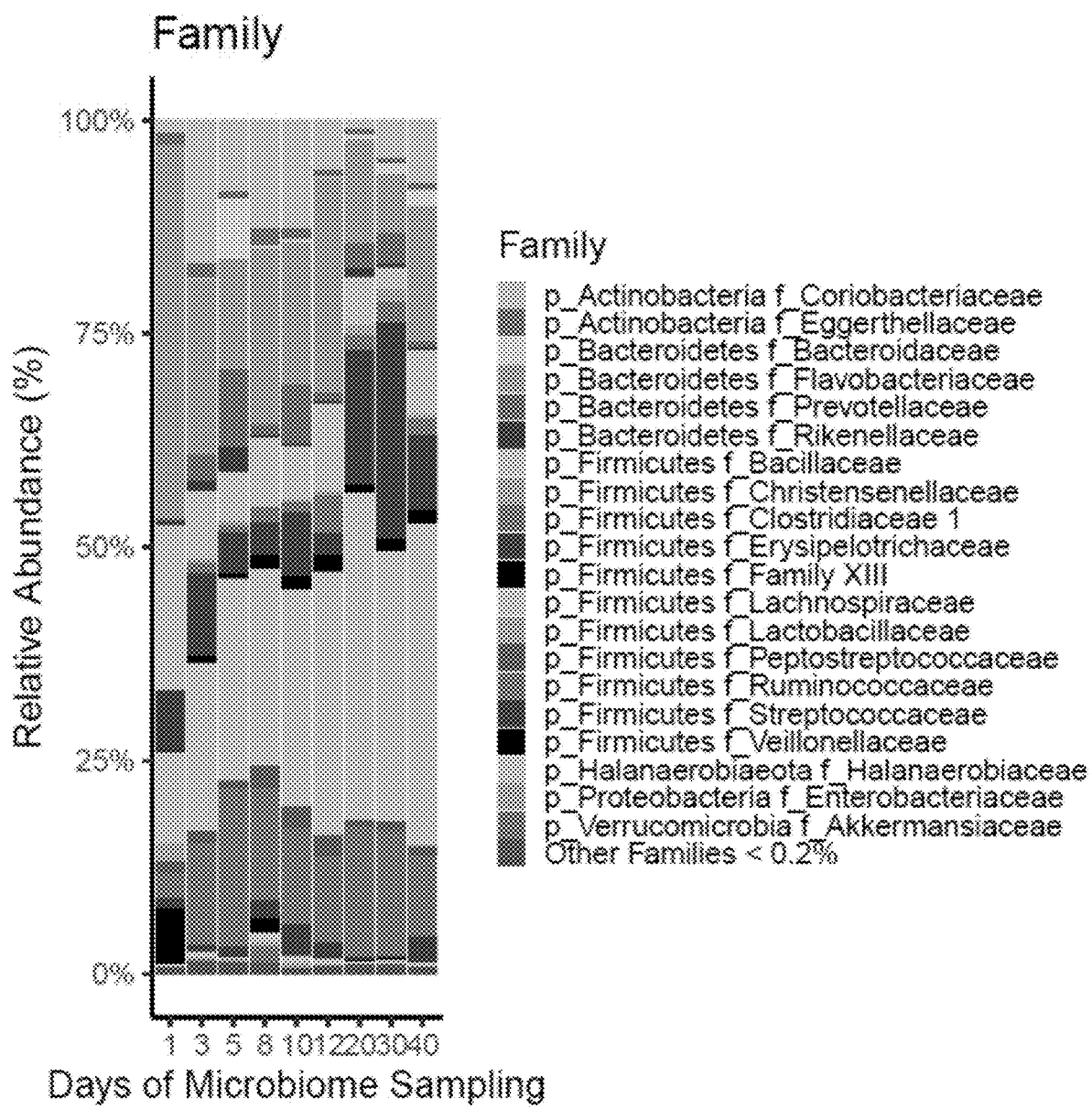

A rapid increase in alpha diversity was noted from baseline samples using both Inverse Simpson and Shannon Index (FIG. 12). Compared to baseline, Inverse Simpson Index diversity increased by 0.14±0.056 points while on ibezapolstat therapy (p=0.017) and by 0.22±0.10 points after EOT (p=0.0033).

Similar results were observed using Shannon Diversity Index; diversity increased by 0.98±0.48 points while on ibezapolstat therapy (p=0.049) and by 1.7±0.87 points after therapy was completed (p=0.043) compared to baseline. Taxa changes during and after ibezapolstat therapy is shown in FIG. 13. A proportional decrease in Bacteroidetes phylum was observed (−10.0±4.8%; p=0.043), most commonly due to a decreased proportion of Bacteroidia class taxa (−10.0±4.8%) and Flavobacteriaceae family taxa (−8.8±4.8%). An increased proportion of Firmicutes phylum was observed (+14.7±5.4%; p=0.009), most commonly due to an increased proportion of Lachnospiraceae (+12.7±6.0%) and Ruminococcaceae (+2.8±2.7%). Other Firmicutes had decreased proportions, most notably Bacillales (−4.4±2.3%) and Lactobacillales (−3.7±2.2%) order taxa. Abundance tables for individual patients are shown in FIG. 15.

Figure 14A:
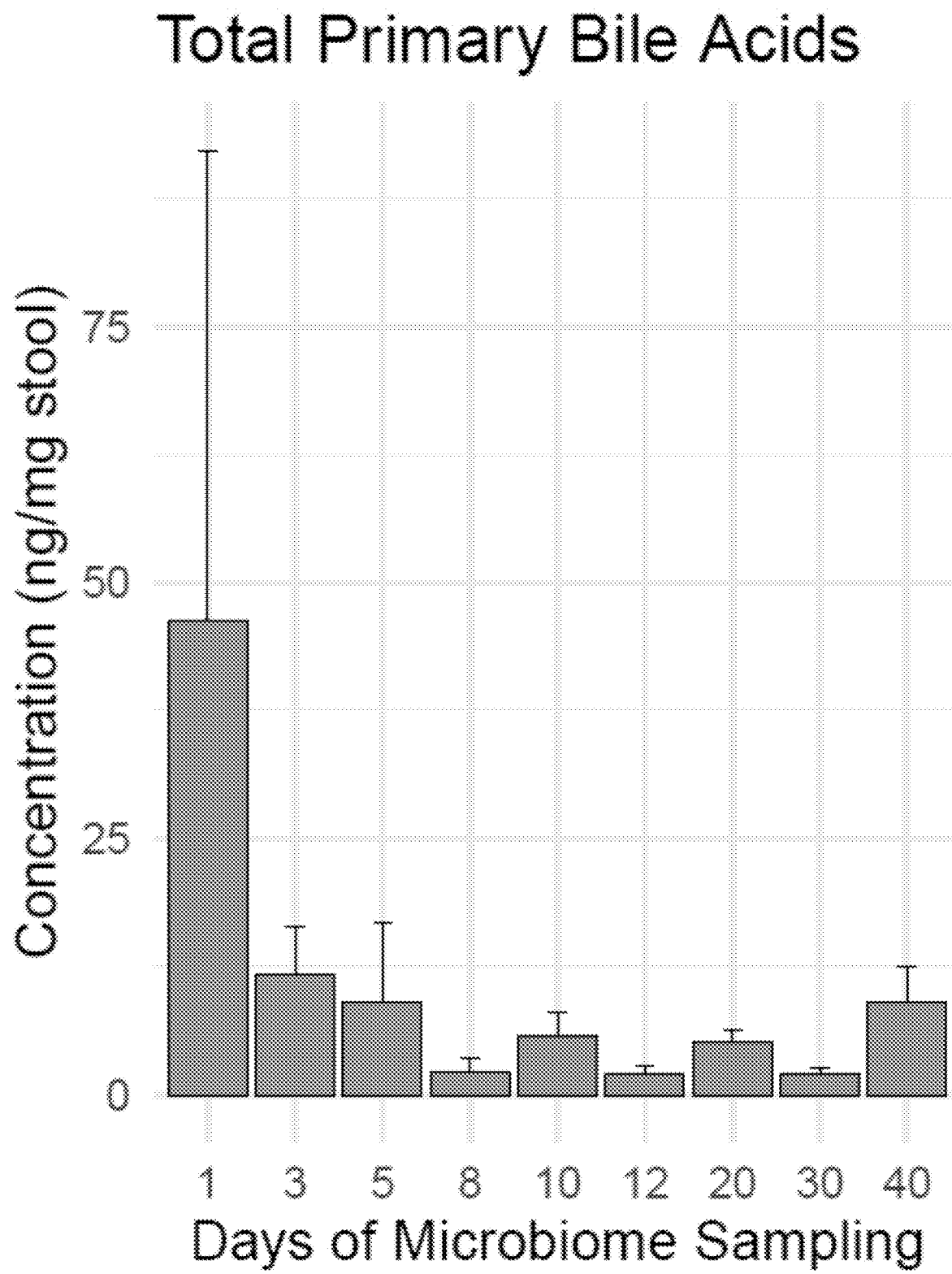
FIG. 14A shows summary of changes with the effects of ibezapolstat over time on primary bile acids.
Figure 14B:
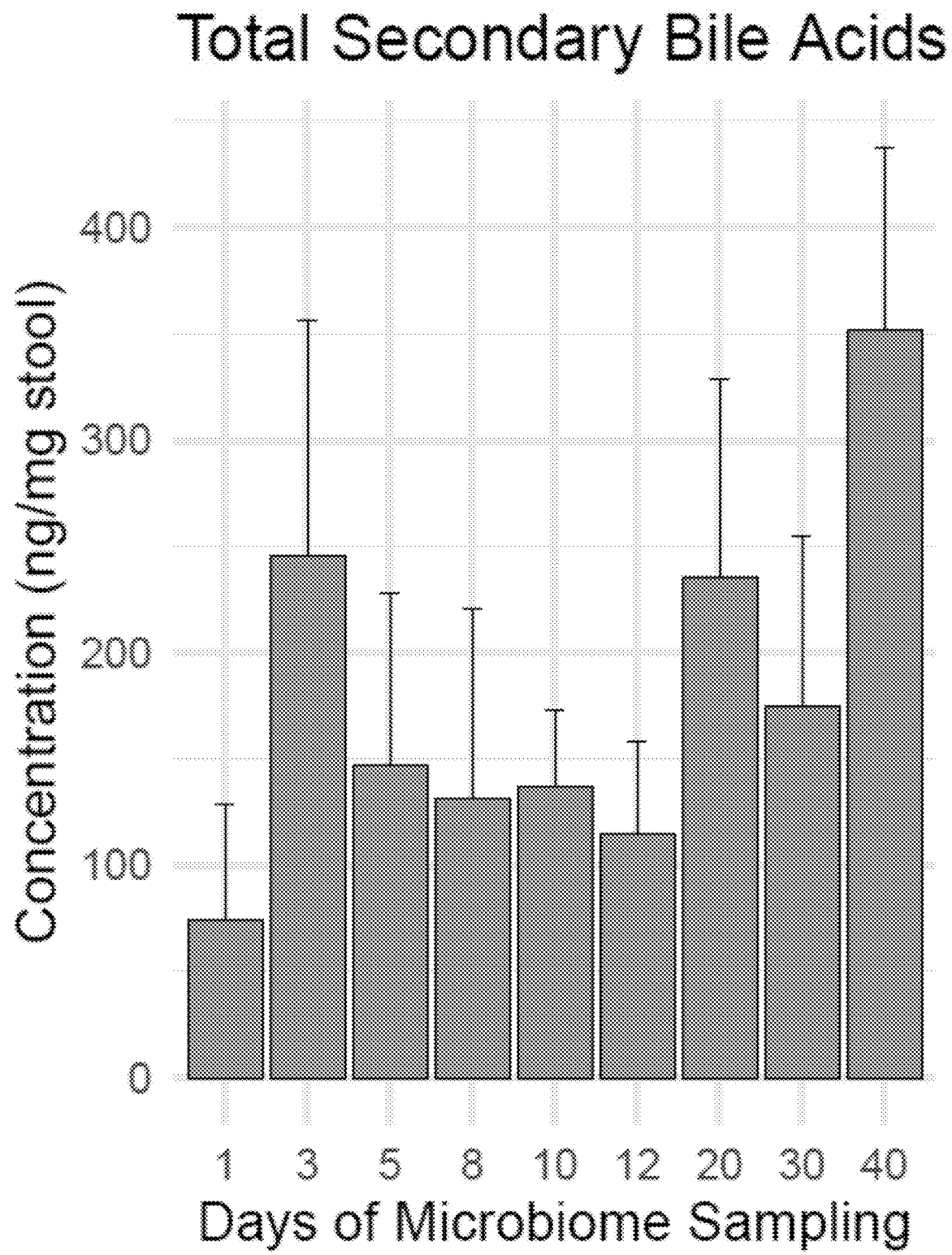
FIG. 14B shows summary of changes with the effects of ibezapolstat over time on secondary bile acids.
Figure 14C:
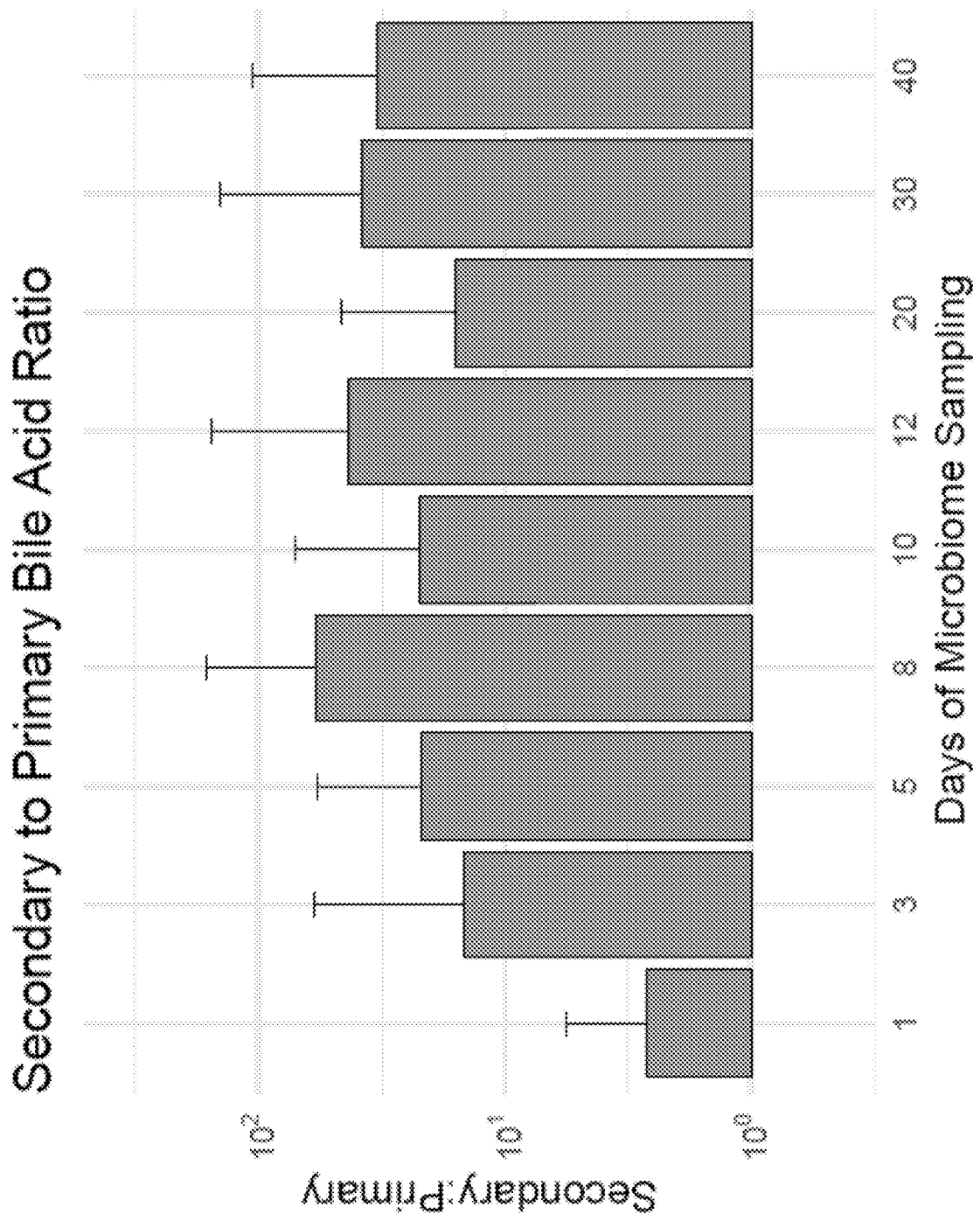
FIG. 14C shows the secondary to primary bile acid ratio. Values represent mean±standard error.
Figure 15A:
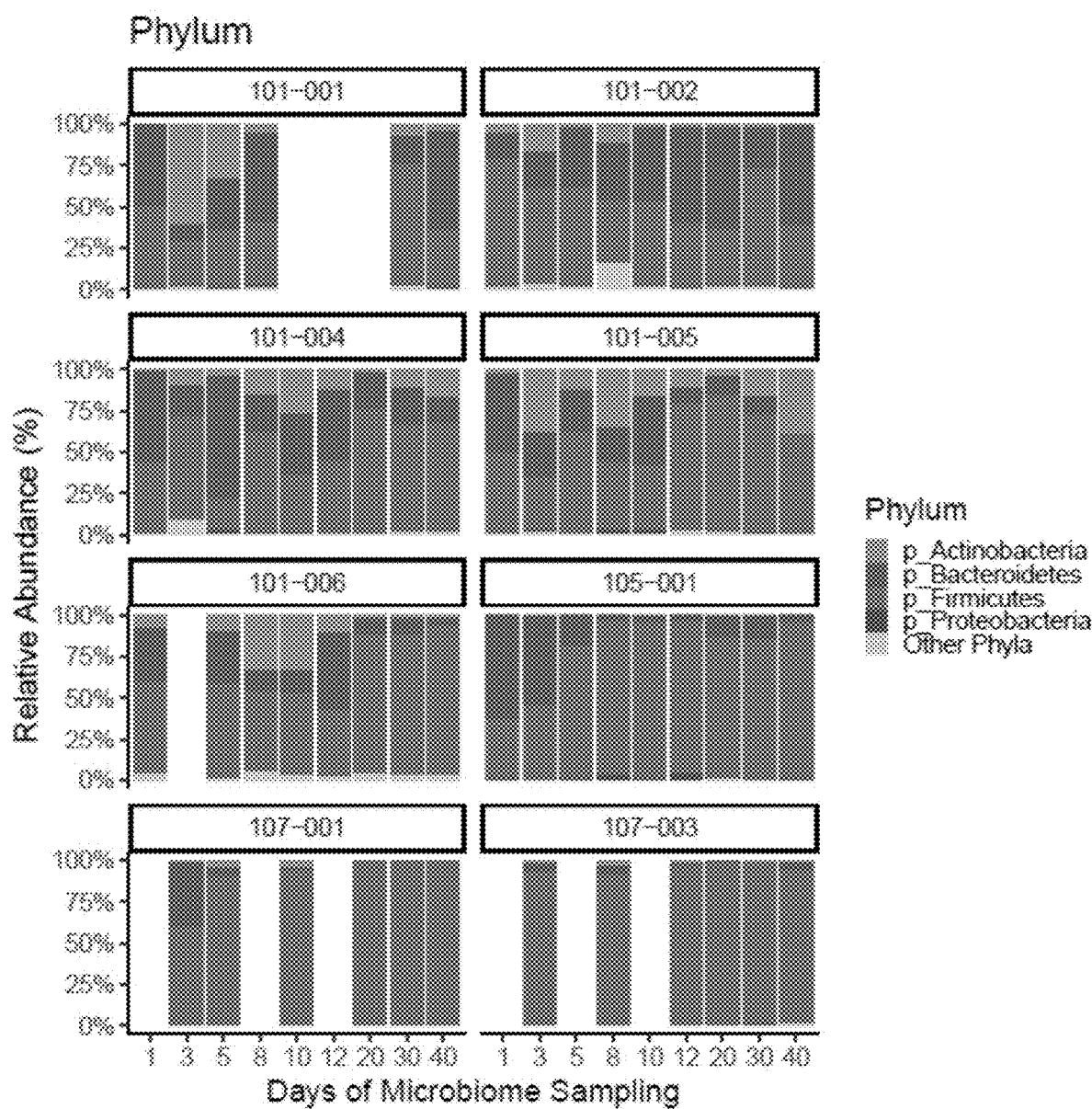
FIG. 15A is a chart showing subject-specific changes in relative abundance of taxa by phylum. The chart represents one patient given a 10-day course of ibezapolstat with follow-up through day 40.
Figure 15B:
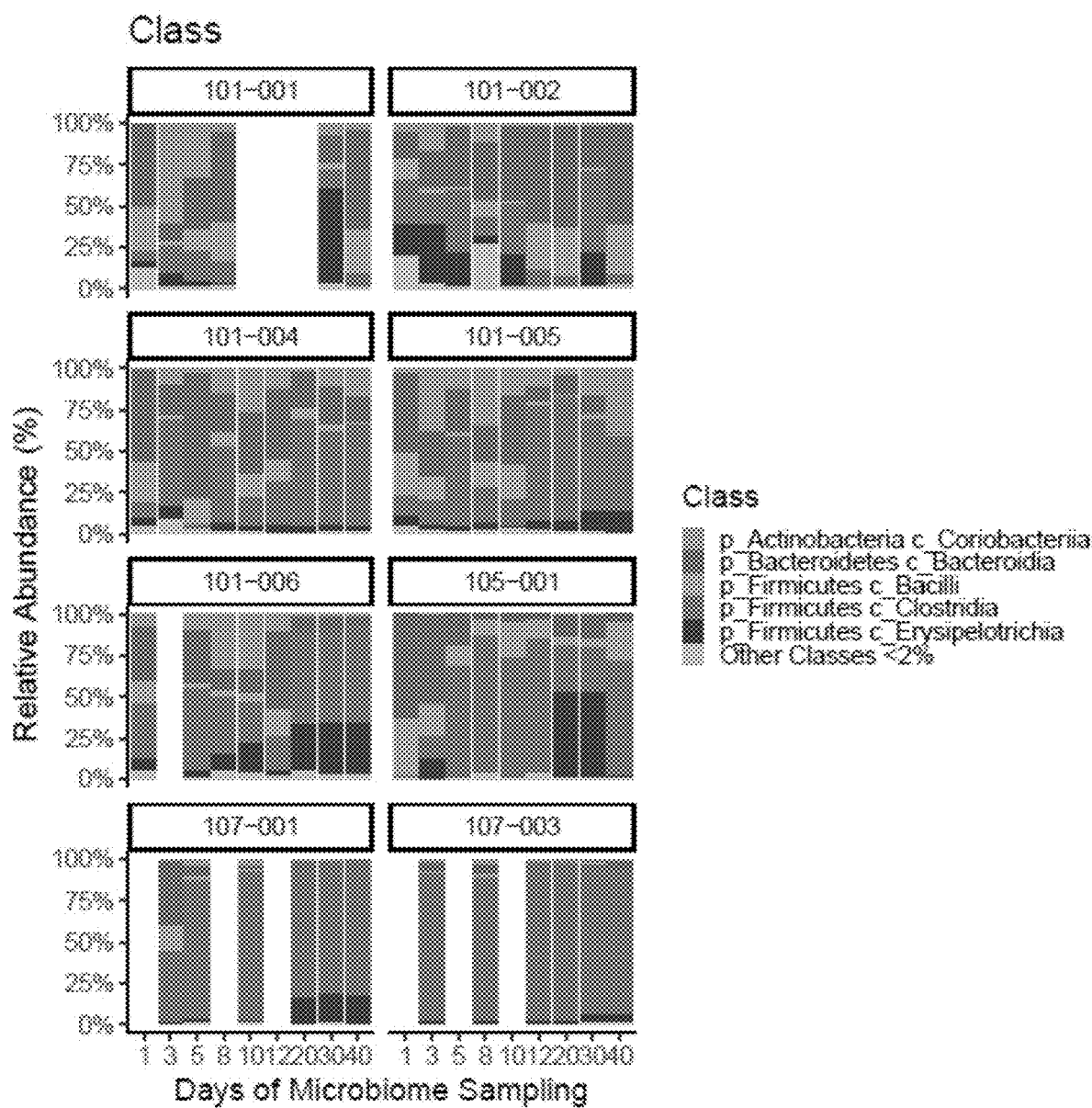
FIG. 15B is a chart showing subject-specific changes in relative abundance of taxa by class. The chart represents one patient given a 10-day course of ibezapolstat with follow-up through day 40.
Figure 15C:
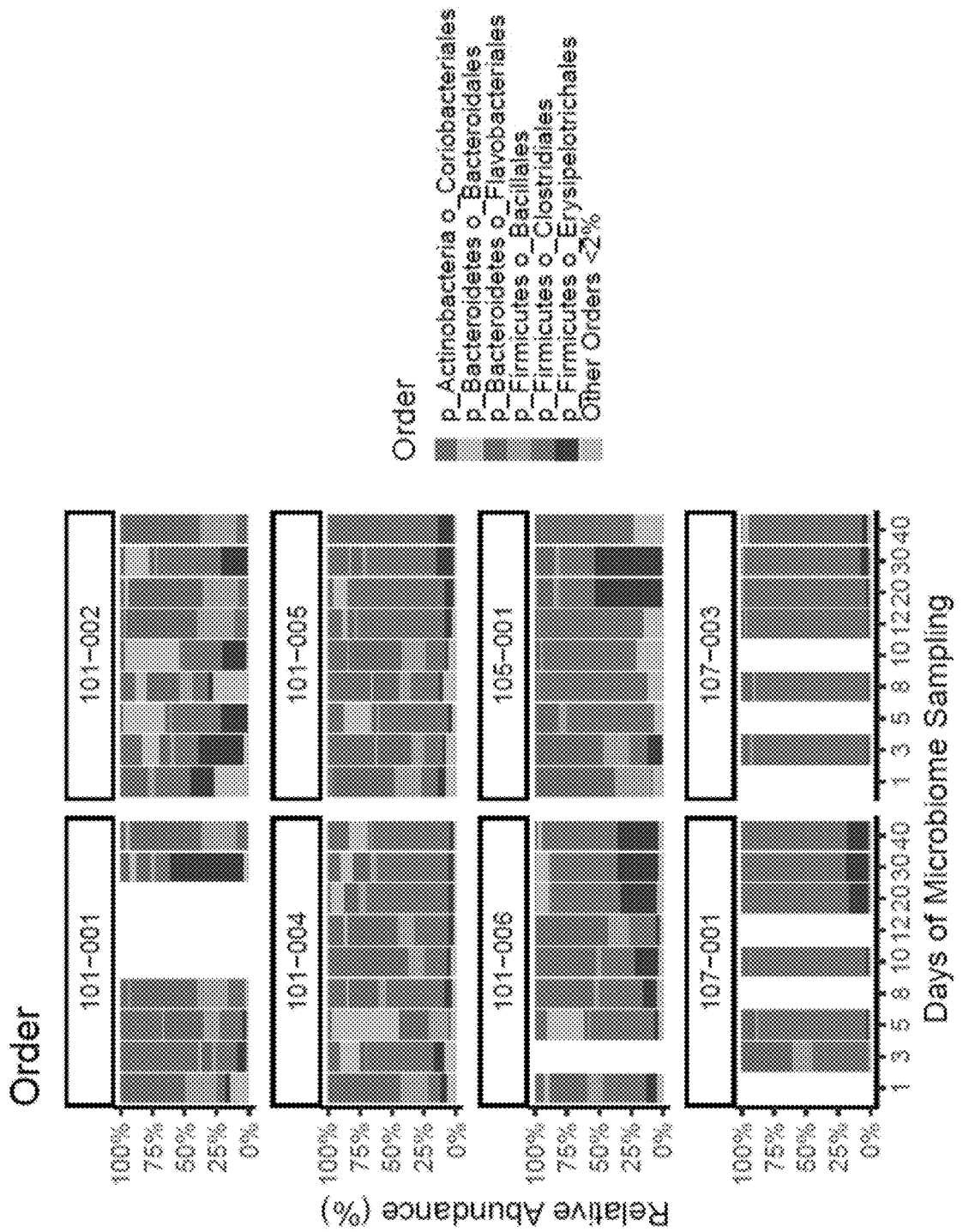
FIG. 15C is a chart showing subject-specific changes in relative abundance of taxa by order. The chart represents one patient given a 10-day course of ibezapolstat with follow-up through day 40.
Figure 15D:
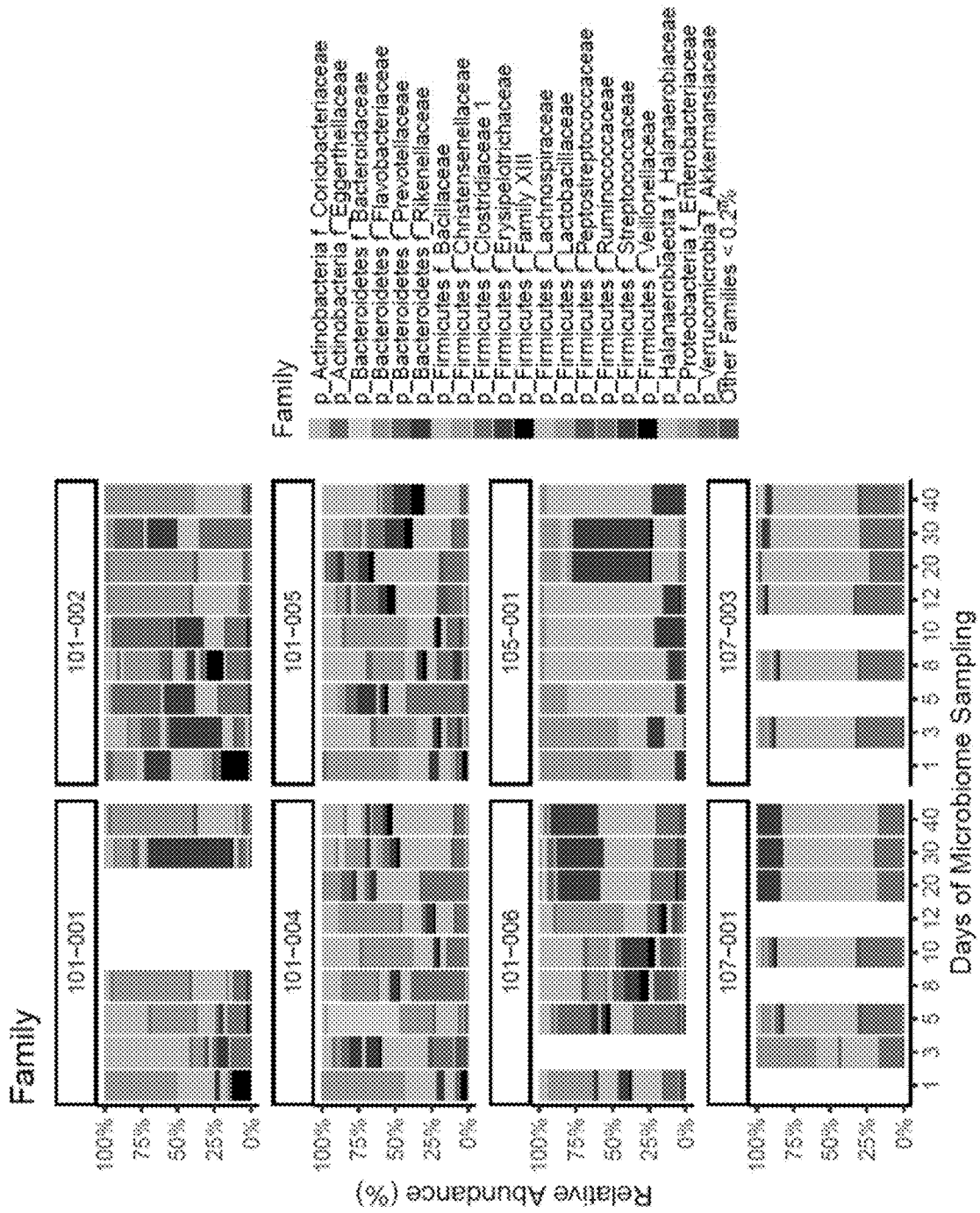
FIG. 15D is a chart showing subject-specific changes in relative abundance of taxa by family. The chart represents one patient given a 10-day course of ibezapolstat with follow-up through day 40.

Results of the bile acid analysis are shown in FIG. 14. Compared to baseline, total primary acids in feces decreased by 40.1±9.6 ng/mg stool during therapy (p=0.0002) and 40.5±14.1 ng/mg stool after completion of therapy (p=0.0066). Compared to baseline, total secondary bile acids increased by 65.6±146.7 ng/mg stool during therapy (p=0.66) and 97.5±215.4 ng/mg stool after completion of therapy (p=0.65).

TABLE 4

Adverse events in CDI patients receiving ibezapolstat

| Adverse event | Frequency | Intensity | Action taken with study medication | Relationship to study drug | Serious AE | Outcome | Treatment required |
|---|---|---|---|---|---|---|---|
| Headache | Intermittent | Mild | No | Unrelated | No | Resolved | No |
| Headache | Intermittent | Mild | No | Unrelated | No | Resolved | No |
| Intertriginous Candidiasis | Continuous | Moderate | No | Unrelated | No | Resolved | Yes |
| Migraine headache | Continuous | Severe | No | Unrelated | No | Resolved | Yes |
| Nausea | Intermittent | Moderate | No | Probably | No | Resolved | No |
| Nausea | Intermittent | Moderate | No | Probably | No | Resolved | No |
| Vomiting | Once | Moderate | No | Probably | No | Resolved | Yes |

The invention claimed is:

1. A method of simultaneously treating a *C. difficile* infection and reducing the likelihood of or preventing the recurrence of *C. difficile* infection in a human subject comprising administering at least about 300 mg to about 1000 mg of ibezapolstat to a subject suffering from a *C. difficile* infection, wherein the administration of ibezapolstat simultaneously treats the *C. difficile* infection and reduces the likelihood or prevents recurrence of *C. difficile* infection within 90 days.

2. The method of claim 1, wherein the administration of ibezapolstat is continued until a clinical cure of the *C. difficile* infection is achieved.

3. The method of claim 1, wherein the administration of ibezapolstat is terminated when a clinical cure of the *C. difficile* infection is achieved.

4. The method of claim 1, wherein the administration of ibezapolstat reduces the likelihood or prevents recurrence of *C. difficile* infection within 30 days.

5. A method of treating a *C. difficile* infection in a subject comprising administering at least about 300 mg to about 1000 mg of ibezapolstat to a human subject suffering from a *C. difficile* infection, wherein the administration of ibezapolstat reduces the recurrence of *C. difficile* infection within 90 days and selectively targets Firmicutes in the gut microbiome of the subject.

6. The method of claim 5, wherein the administration of ibezapolstat results in a different gut microbiome profile compared to the administration of vancomycin.

7. The method of claim 6, wherein the amount of ibezapolstat administered is at least about 300 mg and the amount of vancomycin administered is at least about 125 mg.

8. The method of claim 5, wherein the administration of ibezapolstat is measured by the presence of *C. difficile* toxins in the gut microbiome.

9. The method of claim 5, wherein the administration of ibezapolstat includes an overgrowth of Actinobacteria and Firmicutes phylum species.

10. A method of reducing the likelihood of *C. difficile* infection and/or preventing the recurrence of *C. difficile* infection in a human subject comprising administering at least about 300 mg to about 1000 mg of ibezapolstat to a subject, wherein the administration of ibezapolstat results in a change a reduction in the proportion of Firmicutes to Protobacteria in a gut microbiome, wherein the subject is suffering from a *C. difficile* infection or is susceptible to a recurrence of a *C. difficile* infection and wherein the administration prevents recurrence of *C. difficile* infection within 90 days.

11. The method of claim 10, wherein the prevention of *C. difficile* infection is measured by the proportion of Firmicutes and/or Bacteroidetes to Proteobacteria in the gut microbiome.

12. The method of claim 10, wherein the administration of ibezapolstat results in a greater number of Firmicutes and/or Bacteroidetes in the gut microbiome than in the gut microbiome of subjects treated with vancomycin.

13. The method of claim 12, wherein the amount of ibezapolstat administered is at least about 300 mg and the amount of vancomycin administered is at least about 125 mg.

* * * * *